United States Patent [19]

Tabor et al.

[11] Patent Number: 4,962,020
[45] Date of Patent: Oct. 9, 1990

[54] DNA SEQUENCING

[75] Inventors: Stanley Tabor, Cambridge; Charles C. Richardson, Chestnut Hill, both of Mass.

[73] Assignee: President and Fellows of Harvard College, Cambridge, Mass.

[21] Appl. No.: 218,103

[22] Filed: Jul. 12, 1988

[51] Int. Cl.$^5$ .............................. C12Q 1/68
[52] U.S. Cl. .................... 435/6; 435/803; 435/810; 436/84; 436/501; 436/808; 935/19; 935/76; 935/78
[58] Field of Search .................. 435/6, 92, 183, 810, 435/803; 935/78, 19, 76; 536/27, 127; 436/501, 84, 808

[56] References Cited

U.S. PATENT DOCUMENTS

| | | | |
|---|---|---|---|
| 3,661,893 | 5/1972 | Spiegelman et al. | 260/211.5 |
| 4,072,574 | 2/1978 | Loeb et al. | 195/103.5 |
| 4,707,235 | 11/1987 | Englert et al. | 204/182.8 |
| 4,729,947 | 3/1988 | Middendorf et al. | 435/6 |
| 4,795,699 | 1/1989 | Tabor et al. | 435/6 |
| 4,795,700 | 1/1989 | Dervan et al. | 435/6 |

FOREIGN PATENT DOCUMENTS 265293 2/1981 European Pat. Off. .

OTHER PUBLICATIONS

Bethesda Research Laboratories, "M13 Cloning/-Dideoxy Sequencing, Instruction Manual", pp. 38-60.
Kolodner et al., "Replication of Duplex DNA by Bacteriophage T7 DNA Polymerase and Gene 4 Protein is Accompanied by Hydrolysis of Nucleoside 5′-Triphosphates", Proc. Natl. Acad. Sci. USA, vol. 74, No. 4, pp. 1525-1529, (1977).
Ollis et al., "Domain of E. coli DNA Polymerase I Showing Sequence Homology to T7 DNA Polymerase", Nature, vol. 313, pp. 818-819, (1985).
Harrison, "Two for the Price of One", Nature, vol. 313, pp. 736-737 (1985).
Randahl et al., "An Improved Purification Method and a Physical Characterization of Phage T7 DNA Polymerase", Eur. J. Biochem. 128, pp. 445-449 (1982).
Nordstrom et al., "Characterization of Bacteriophage T7 DNA Polymerase Purified to Homogeneity by Antithioredoxin Immunoadsorbent Chromatography", Journal of Biological Chemistry, vol. 256, No. 6, pp. 3112-3117 (1981).
Fuller et al., "Initiation of DNA Replication at the Primary Origin of Bacteriophage T7 by Purified Proteins", Journal of Biological Chemistry, vol. 260, No. 5, pp. 3185-3196, 1985.
McClure et al., "The Kinetics and Processivity of Nucleic Acid Polymerases", Methods in Enzymology, vol. 64, pp. 277-297, 1980.
Watson et al., "Recombinant DNA", Cold Spring Harbor Laboratory, 1983.
Wilkins, "Site-Specific Analysis of Drug Interactions and Damage in DNA Using Sequencing Techniques", Analytical Biochem., 147: 267-279, 1985.
Tabor et al., Proc. Natl. Acad. Sci., USA, 84, 4767-4771 (1987).
United States Biochemical Corporation Booklet, Sequenase, 1987.
United States Biochemical Corporation, Editorial Comments, vol. 14 (1987).

(List continued on next page.)

Primary Examiner—Amelia Burgess Yarbrough
Attorney, Agent, or Firm—Fish & Richardson

[57] ABSTRACT

A method for sequencing a strand of DNA, including the steps of: providing the strand of DNA; annealing the strand with a primer able to hybridize to the strand to give an annealed mixture; incubating the mixture with a deoxyribonucleoside triphosphate, a DNA polymerase, and a chain terminating agent under conditions in which the polymerase causes the primer to be elongated to form a series of DNA products differing in length of the elongated primer, each DNA product having a chain terminating agent at its elongated end; the number of each DNA product being approximately the same for substantially all DNA products differing in length from 1 to 20 bases.

34 Claims, 11 Drawing Sheets

OTHER PUBLICATIONS

Sanger et al., J. Mol. Biol. 94, 441 (1975).
Mills et al., Proc. Natl. Acad. Sci. 76, 2232 (1979).
Maat et al., Nucl. Acid. Res. 5, 4537 (1978).
United States Biochemicals Advertisement, Extend the Limits of Sequencing with SEQUENASE (1987).
United States Biochemicals Advertisement, DNA Sequencing SEQUENASE (1987).
Kristensen et al., "T7 DNA Polymerase in Automated Dideoxy Sequencing", Nucleic Acids Research, vol. 16, No. 8, 3487–3496, 1988.
Wong et al., "Characterization of β-thalassaemia Mutations Using Direct Genomic Sequencing of Amplified Single Copy DNA", Nature, vol. 330, 19087.
Johnston-Dow, et al., "Optimized Methods for Fluorescent and Radio Labelled DNA Sequencing", Biotechniques, 5(8): 754–765 (1987).
Rabussay, et al., "Electroporation of Mammalian and Plant Cells", Focus, 9(3), 1987.
BRL Catalog, "You Be the Judge".
McGraw, "Dideoxy DNA Sequencing with End-Labeled Oligonucleotide Primers", Analytical Biochemistry, 143: 298–303 (1984).
Hong, "Sequencing of Large Double-Stranded DNA Using the Dideoxy Sequencing Technique", Bioscience Reports, 2: 907–912, 1982.
Sanger, et al., "Use of DNA Polymerase 1 Primed by a Synthetic Oligoneucleotide to Determine a Nucleotide Sequence in Phage f1 DNA", Proc. Natl. Acad. Sci., USA, vol. 70, No. 4, pp. 1209–1213 (1973, April).
Sanger et al., "Cloning in Single-Strand Bacteriophage as an Aid to Rapid DNA Sequencing", J. Mol. Biol., 143, pp. 161–178 (1980).
Sanger et al., "The Use of Thin Acrylamide Gels for DNA Sequencing", FEBS Letters, vol. 87(1): 107–110, 1978.
Zagursky, et al., "Rapid and Easy Sequencing of Large Linear Double-Stranded DNA and Supercoiled Plasmid DNA", Gene Anal. Techn., 2:89–94 (1985).
Maxam and Gilbert, "A New Method for Sequencing DNA", Proc. Natl. Acad. Sci., USA, vol. 74, No. 2, pp. 560–564 (Feb., 1977).
Pharmacia-Mol. Biology Div., "Dideoxy Sequencing of Plasmid DNA"; FPLC Pure, AMV Reverse Transcriptase Applications.
Beck, "Colorimetric-Detected DNA Sequencing", Anal. Bioch. 164:1–7 (1987).
Agellon and Chen, "Supercoiled Plasmid Sequencing", Gene Anal. Techn. 3:86–89 (1986).
Bartlett, et al., "Sequencing of Supercoiled Plasmid DNA", BioTech., vol. 4, No. 3, pp. 208–210 (1986).
Pharmacia, "For Sequencing Genomes, Or Just Kilobase", vol. 16, No. 1, pp. 1–3.
Church & Gilbert, Proc. Natl. Acad. Sci., USA, 81:1991 (1984).
Ambrose et al., "Sequence Analysis of End-Labeled DNA Fragments by Solvolysis in Hot Aqueous Piperidine Solutions", Anal. Biochem. 169, 151–158, (1988).
Ambrose et al., "Analysis of DNA Sequences Using a Single Chemical Cleavage Procedure", Biochemistry, vol. 24, No. 22, 6194–6200, (1985).
Ambrose et al., "One-Lane Sequence Analysis of Oligodeoxyribonucleotides", Anal. Biochem., vol. 159, 24–28, (1986).
Mills and Kramer, "Structure-Independent Nucleotide Sequence Analysis", Proc. Natl. Acad. Sci., USA, vol. 76, No. 5, 2232–2235, (1979).
Barnes, "Sequencing DNA with Dideoxyribonucleotides as Chain Terminators: Hints and Strategies for Big Projects", Methods in Enzymology, vol. 152, pp. 538–556, 1987.
Ambrose et al., "DNA Sequencing: Chemical Methods", Methods in Enzymology, vol. 152, pp. 552–537, 1987.
Pharmacia, "Sequencing Kit".
Axelrod et al., "Transcription from Bacteriophage T7 and SP6 RNA Polymerase Prompters in the Presence of 3'-Deoxyribonucleoside 5'-Triphosphate Chain Terminators", Biochemistry, 24:5716–5723, 1985.
Hoog et al., "Nucleotide sequence of the thioredoxin gene from E. coli", Bioscience Reports 4:917–923, 1984.
Bina-Stein et al., "Rapid sequence determination of late simian virus 40 16S mRNA leader by using inhibitors of reverse transcriptase", Proc. Natl. Acad. Sci. USA, 76:731–735, 1979.
Smith, "DNA Sequence Analysis by Primed Synthesis", Methods in Enzymology, vol. 65, pp. 560–580, 1980.
Barrell, "Sequence Analysis of Bacteriophage φX174

(List continued on next page.)

OTHER PUBLICATIONS

DNA", Biochemistry of Nucleic Acids II, vol. 17, pp. 125–133, 1978.

Detera et al., "Studies on the Mechanism of E. coli DNA Polymerase 1 Large Fragment", J. Biol. Chem., 257:9770–9780, 1982.

Kornberg, "DNA Replication", W. H. Freeman & Company, pp. 87–100, 116–124, 127–129, 405, 655–661, 1974.

Banker, "Advances in Dideoxy Sequencing", 72 Bio-Techniques, 1984.

Engler, "Bacteriophage T7 DNA Replication", J. Biol. Chemistry, 258:11197, 1983.

"DNA Sequencing Method Uses Thioesters", C&EN, (1988).

*Nucleic Acids Research*, Rientiz et al., vol. 13, No. 15, (1985).

*Nucleic Acids Research*, Hillebrand et al., vol. 12, No. 7, (1984).

"On the Enzymatic Basis for Mutagenesis by Manganese", Goodman et al., *The Journal of Biological Chemistry*, pp. 3469–75, (1983).

"Metal-induced Infidelity of DNA Synthesis", Zakour et al, J. Cancer Res. Clin. Oncol, (1981), 99:187–196.

"Processive Nature of Reverse Transcription by Avian Myeloblastosis Virus Deoxyribonucleic Acid Polymerase", Gregerson et al., *Biochemistry*, pp. 301–306, (1980).

"Inhibition of Deoxyribonucleic Acid Polymerases of Human Leukemic Leukocytes by 2',3'-Dideoxythymidine Triphosphate", Allaudeen, *Biochemical Pharmacology*, vol. 29, pp. 1149–1153, (1980).

"On the Fidelity of DNA Replication", *The Journal of Biological Chemistry*, Sirover et al., pp. 107–111, (1979).

"On the Fidelity of DNA Replication", Kunkel et al., *The Journal of Biological Chemistry*, vol. 254, No. 13, p. 5817, (1979).

"Differences in the Effects of Manganese and Magnesium on Initiation and Elongation in the RNA Polymerase I Reaction", Nagamine et al., *Biochimica et Biophysica Acta*, 519, (1978), 440–446.

"Effect of Metal Cations on Misincorporation", Miyaki et al., *Biochemical and Biophysical Research Communications*, vol. 77, No. 3, (1977).

"DNA Sequencing with Chair-Terminating Inhibitors", *J. Natl. Acad. Sci.*, vol. 74, No. 12, pp. 4563–5467, (1977), Sanger et al.

"Effect of $Mn^{2+}$ on the In Vitro Activity of Human Deoxyribonucleic Acid Polymerase Beta", Wang et al., *Biochemistry*, vol. 16, No. 22, (1977), pp. 4927–4934.

"The Effect of Magnesium and Manganese Ions on the Structure and Template Activity for Reverse Transcriptase of Polyribocytidylate and its 2'-o-Methyl Derivative", Vamvakopoulos et al., *Nucleic Acids Research*, vol. 4, No. 10, (1977), pp. 3589–3597.

"On the Fidelity of DNA Replication", *The Journal of Biological Chemistry*, vol. 252, No. 11, (1977), pp. 3605–3610.

"Effects of $Mn^{++}$ and $Mg^{++}$ on Activity of Human DNA Polymerase Beta", Eichler et al., *Federation Proceedings*, vol. 36, No. 1, (1977), p. 848.

"Metal Activation of DNA Synthesis", Sirover et al., *Biochemical and Biophysical Research Communications*, vol. 70, No. 3, (1976), pp. 812–817.

"Escherichia Coli DNA Polymerases II and III: Activation by Magnesium or by Manganous Ions", *Biochimica et Biophysica Acta*, 447, (1976), pp. 175–187, Helfman et al.

"Multiple Enzyme-Manganese—Nucleotide Complexes of E. Coli DNA Polymerase I", Tamir et al., *Federation Proceedings*, vol. 31, No. 1. (1972), p. 912Abs.

"The Differential Effect of Magnesium and Manganese Ions on the Synthesis of Poly (dGdC) and Micrococcus Luteus DNA by Micrococcus Luteus DNA Polymerase", *J. Mol. Biol.*, (1971), 61, 1–23, Litman.

"Enzymatic Synthesis of Deoxyribonucleic Acid", *The Journal of Biological Chemistry*, vol. 244, No. 11, (1969), pp. 3019–3028, Deutscher et al.

*DNA Replication*, Kornberg, pp. 125–126, Chapter 4: DNA Polymerase I of *E. coli*.

"Effect of Variations in the Conditions of DNA Synthesis Upon the Accuracy of DNA Replication", Razzaki et al., *Genetic Consequences of Nucleotide Pool Imbalance*, pp. 175–187.

DNA Replication, Kornberg, pp. 125–126, Chapter 4: DNA Polymerase I of *E. coli*.

"Effect of Variations in the Conditions of DNA Synthesis Upon the Accuracy of DNA Replication", Razzaki et al., Genetic Consequences of Nucleotide Pool Imbalance, pp. 175–187.

(List continued on next page.)

OTHER PUBLICATIONS

DNA Replication, Kornberg, pp. 150–151, Chapter 4: DNA Polymerase 1 of *E. coli.*

Berg et al., "The Synthesis of Mixed Polynucleotides Containing Ribo- and Deoxyribonucleotides by Purified Preparations of DNA Polymerase from *E. coli.,* Informational Macromolecules (Symposium), pp. 467–483, (1963).

Barnes, "DNA Sequencing by Partial Ribosubstitution", J. Mol. Biol., (1978), 119, 83–99.

van de Sande et al., "Studies on Polynucleotides", J. Biol. Chemistry, vol. 247, No. 19, pp. 6140–6148, (1972).

Salser et al., "Nucleotide Sequencing of DNA: Preliminary Characterization of the Products of Specific Cleavages at Guanine, Cytosine, or Adenine Residues", Proc. Natl. Acad. Sci. 69:1, pp. 238–242, (1972).

Gish et al., "DNA and RNA Sequence Determination Based on Phosphorothioate Chemistry", Science, vol. 240, pp. 1520–1522, (1988).

"DNA Sequencing Method Uses Thioesters", *C&EN,* (1988).

*Nucleic Acids Research,* Rientiz et al., vol. 13, No. 15, (1985).

*Nucleic Acids Research,* Hillebrand et al., vol. 12, No. 7, (1984).

"On the Enzymatic Basis for Mutagenesis by Manganese", Goodman et al., *The Journal of Biological Chemistry,* pp. 3469–75, (1983).

"Metal-Induced Infidelity of DNA Synthesis", Zakour et al, J. Cancer Res. Clin. Oncol (1981), 99:187–196.

"Processive Nature of Reverse Transcription by Avian Myeloblastosis Virus Deoxyribonucleic Acid Polymerase", Gregerson et al., *Biochemistry,* pp. 301–306, (1980).

"Inhibition of Deoxyribonucleic Acid Polymerases of Human Leukemic Leukocytes by 2',3'-Dideoxythymidine Triphosphate", Allaudeen, *Biochemical Pharmacology,* vol. 29, pp. 1149–1153, (1980).

"On the Fidelity of DNA Replication", *The Journal of Biological Chemistry,* Sirover et al., pp. 107–111, (1979).

"On the Fidelity of DNA Replication", Kunkel et al., *The Journal of Biological Chemistry,* vol. 254, No. 13, p. 5718, (1979).

"Differences in the Effects of Manganese and Magnesium on Initiation and Elongation in the RNA Polymerase I Reaction", Nagamine et al., *Biochimica et Biophysica Acta,* 519, (1978), 440–446.

"Effect of Metal Cations on Misincorporation", Miyaki et al., *Biochemical and Biophysical Research Communications,* vol. 77, No. 3, (1977).

"DNA Sequencing with Chain-Terminating Inhibitors", *J. Natl. Acad. Sci.,* vol. 74, No. 12, pp. 4563–5467, (1977), Sanger et al.

DNA SEQUENCING

BACKGROUND OF THE INVENTION

This invention was made with government support including a grant from the U.S. Public Health Service, contract number AI-06045. The U.S. government has certain rights in the invention.

This invention relates to DNA sequencing and in particular to automated methods for DNA sequencing.

DNA sequencing is generally carried out by the method of Sanger et al. (Proc. Nat. Acad. Sci. USA 74:5463, 1977) and involves enzymatic synthesis of single strands of DNA from a single stranded DNA template and a primer. Referring to FIG. 1, four separate syntheses are carried out. A single stranded template is provided along with a primer which hybridizes to the template. The primer is elongated using a DNA polymerase, and each reaction terminated at a specific base (guanine, G, adenine, A, thymine, T, or cytosine, C) via the incorporation of an appropriate chain terminating agent, for example, a dideoxynucleotide. Enzymes currently used for this method of sequencing include: the large fragment of *Escherichia coli* DNA polymerase I ("Klenow" fragment), reverse transcriptase, Taq polymerase, and a modified form of bacteriophage T7 DNA polymerase.

Still referring to FIG. 1, the four DNA synthesis reactions result in formation of four series of DNA products, each product having one defined terminus and one variable terminus. The defined terminus starts with the primer molecule. The variable terminus ends with a chain terminating agent specific for the nucleotide base (either G, A, T, or C) at which the synthesis reaction terminated. The four different series of products are each separated on the basis of their molecular weight, in four separate lanes in a high resolution polyacrylamide gel, to form four series of bands, with each band on the gel corresponding sequentially to a specific nucleotide in the DNA sequence. Thus, the relative positions of the bands identify the positions in the DNA sequence of each given nucleotide base. Generally, the DNA products are labelled so that the bands produced are readily detected. As shown in FIG. 1, the intensity of the bands is generally non uniform, within a single lane, because band intensity is directly related to the total number or concentration of DNA products of the same molecular weight in a specific lane, and this number varies from one product to another even when they are of approximately the same molecular weight and even when they contain the same chain terminating agent.

Using the above methodology, automated systems for DNA sequence analysis have been developed. One instrument, manufactured by EG&G, uses a $^{32}$P-label and a DNA polymerase, and the resulting DNA products separated by gel electrophoresis. Toneguzzo et al, 6 Biotechniques 460, 1988. A $^{32}$P-detector at the bottom of the gel scans for radioactivity as it passes through the bottom of the gel Four synthesis reactions are required for each template to be sequenced, as well as four lanes on each gel, a separate lane being used for products terminated by each specific chain terminating agent, as shown for example in FIG. 1.

Kanbara et al , 6 Biotechnology 816, 1988, have replaced the $^{32}$P-labelled primer, described above, with a fluorescent-labelled primer The resulting fluorescently labelled products are excited with a laser at the bottom of the gel and the fluorescence detected with a CRT monitor. This procedure also requires four synthesis reactions and four lanes on the gel for each template to be sequenced.

Applied Biosystems manufactures an instrument in which four different primers are used, each labelled with a different fluorescent marker. Smith et al., 13 Nuc. Acid. Res. 2399, 1985; and 321 Nature 674, 1986. Each primer is used in a separate reaction containing one of four dideoxynucleotides. After the four reactions have been carried out they are combined together and run in a single lane on a gel. A laser at the bottom of the gel is used to detect fluorescent products after they have been permeated or electrophoresed through the gel. This system requires four separate annealing reactions and four separate synthesis reactions for each template, but only a single lane on the gel. Computer analysis of the sequence is made easier by having all four bands in a single lane.

DuPont provides an instrument in which a different fluorescent marker is attached to each of four dideoxynucleoside triphosphates. Prober et al., 238 Science 336, 1987. A single annealing step, a single polymerase reaction (containing each of the four labelled dideoxynucleosides triphosphates) and a single lane in the sequencing gel are required. The four different fluorescent markers in the DNA products are detected separately as they are electrophoresed through the gel.

Englert et al., U S. Pat. No. 4,707,237 (1987), describes a multichannel electrophoresis apparatus having a detection means, disposed substantially across the whole width of the gel, which can sense labelled DNA products as they migrate past the detector means in four separate lanes, and identifies the channel or lane in which the sample is located. Preferably, radioisotopic labels are used.

Inherent to procedures currently used for DNA sequence analysis is the necessity to separate either radioactively or fluorescently-labelled DNA products by a gel permeation procedure such as polyacrylamide or other gel electrophoresis, and then detect their locations relative to one another along the axis of permeation or movement through the gel. The accuracy of this procedure is determined in part by the uniformity of the signal in bands which have permeated approximately the same distance through the gel. Differences or variations in signal intensities between nearby bands create several problems. First, they decrease the sensitivity of the method, which is limited by the ability to detect the bands containing the weakest signals. Second, they create difficulties in determining whether a band with a weak signal is a true signal due to the incorporation of a chain terminating agent, or an artifact due to a pause site in the DNA, where the polymerase has dissociated. Third, they decrease the accuracy in determining the DNA sequence between closely spaced bands since the strong signal of one band may mask the weak signal of its neighbor.

SUMMARY OF THE INVENTION

All of the foregoing problems are overcome in the present invention, where approximately the same amounts of DNA products of similar molecular weights are produced in a sequencing reaction, and thus nearby bands in the sequencing gel, in the same lane, are of approximately the same intensity.

The ability to produce nearby bands of approximately the same intensity is useful since it permits the results of any sequencing reaction to be read more easily and with greater certainty. Further, since the DNA products from a sequencing reaction with a specific chain terminating agent form bands which are of approximately the same intensity as that of nearby bands, band intensity itself provides a specific label for the series of bands so formed. The number of DNA products of approximately the same molecular weight produced by a given chain terminating agent varies depending upon the concentration of the chain terminating agent. Thus, by using a different concentration of each of the four chain terminating agents for the synthesis, the DNA products incorporating one chain terminating agent are distinguished from DNA products of approximately the same molecular weight incorporating other chain terminating agents in that they differ in number or amount; consequently, the bands of DNA products can be identified as to chain terminating agent simply by their intensity as compared to the intensities of nearby bands. As a result, two or more series of DNA products, each series having a different chain terminating agent, can be subjected to gel permeation in a single lane and identified, i.e., distinguished from each other, by the intensity of each band as compared to the intensity of nearby bands. Moreover, the syntheses of DNA products incorporating different chain terminating agents need not be carried out separately, in separate containers, but may all be carried out simultaneously in a single reaction vessel, and the same label, e.g., radioisotopic, fluorescent, etc. can, if desired, be used for all chain terminating agents instead of a different label for each, thus simplifying the procedure.

It should be noted, however, that there is a gradual decrease in intensity of all bands of DNA products as they permeate through the gel, those that have travelled the shortest distance displaying less intensity than those which have travelled the farthest distance. Neverless, the relative intensity of each band as compared to nearby bands at any location along the axis of permeation remains approximately the same throughout. This conservation of relative intensity throughout the extent of permeation makes possible the present invention.

By "nearby bands" is meant those in the same lane within about 20–30 mm either ahead of or behind the band in question, measured along the axis of permeation. In general, the nearby bands include DNA products differing from the one in question by no more than 20 bases (i.e., with a mass differing by no more than about 6,000 daltons).

In general, the invention features a DNA polymerase for use in DNA sequencing reactions, which, in a sequencing reaction, causes DNA products of slightly different molecular weight to be produced in approximately equal numbers. Thus, when such DNA products are separated in a gel matrix they form bands, with nearby bands being of approximately the same intensity. Without being bound to any particular theory, the inventors regard this uniformity in intensity as being due to the polymerase not discriminating between normal nucleoside triphosphates and chain terminating agents, such as dideoxynucleoside triphosphates.

In a first aspect, the invention features a method for sequencing a strand of DNA, including the steps of: providing the strand of DNA; annealing the strand with a primer able to hybridize to the strand to give an annealed mixture; incubating the annealed mixture with a deoxyribonucleoside triphosphate, a DNA polymerase, and a first chain terminating agent under conditions in which the polymerase causes the primer to be elongated to form a first series of first DNA products differing in length of the elongated primer, each first DNA product having a chain terminating agent at its elongated end; the number of each first DNA product being approximately the same for substantially all DNA products differing in length from 1 to 20 bases. Preferably, the method further includes the steps of: separating the first DNA products by gel permeation according to molecular weight to form a first series of bands, each first series band representing a first DNA product of a given molecular weight, wherein the intensity of each nearby first series band is approximately the same for substantially all first series bands; and determining the position of each first band.

By "substantially all" is meant that at least 9 out of 10 (or 19 out of 20) nearby bands have approximately the same intensity. That is, only occasional bands will have a different intensity. This different intensity results from artifacts. One example of such an artifact is the compression of two or more DNA products of different molecular weight within one band. The result of two such compressions are shown in FIG. 2 where the artifactual bands are marked with an asterisk. By approximately the same is meant that band intensity varies by at most 2 fold, most preferably at most 1.2 fold. By gel permeation is meant to include existing polyacrylamide gels used for DNA sequencing, and any other mechanism for separating DNA products according to their molecular weight.

In one embodiment, production of nearby bands of approximately the same intensity is achieved by incubating a DNA polymerase in a solution containing manganese or iron ions.

In one preferred embodiment, the method further includes the steps of providing a second chain terminating agent in the annealed mixture at a concentration different from the first chain terminating agent, wherein the DNA polymerase causes production of a second series of second DNA products, each second DNA product having the second chain terminating agent at its elongated end, the number of each second DNA product being approximately the same for substantially all DNA products differing in length from 1 to 20 bases, wherein the number of substantially all the first and all the second DNA products differing in length from 1 to 20 bases is distinctly different. Most preferably, the second series of second DNA products form a second series of bands when separated by gel permeation according to molecular weight, wherein the intensity of substantially all nearby second series bands is approximately the same, and the intensity of substantially all bands of the first series is distinctly and distinguishably different from the intensity of each nearby band of the second series, and the method further includes the step of determining the position and intensity of each band, the intensity being representative of a particular band series.

By distinctly different is meant that a band of one series can be distinguished from a nearby band (i.e., a band with a length differing from 1 to 20 bases) in the other series. That is, a machine which measures the number of DNA products of a specific molecular weight can distinguish the two series of DNA products from each other.

In another preferred embodiment, the method includes providing two other chain terminating agents wherein the polymerase causes production of a second and third series of second and third DNA products, the number of each second and third DNA products being approximately the same for substantially all DNA products differing in length from 1 to 20 bases, wherein the number of substantially all the first, all the second and all the third DNA products differing in length from 1 to 20 bases is distinctly different. Most preferably, each second and third series of the second and third DNA products form a different series of second and third bands, when separated by gel permeation according to molecular weight, wherein the intensity of substantially all nearby second series bands is approximately the same, the intensity of substantially all nearby third series bands is approximately the same, and wherein the intensity of substantially all nearby bands of different series is distinctly different; and the method further includes the steps of determining the position and intensity of each band, the intensity being representative of a particular band series.

In yet another preferred embodiment, the method includes providing in the annealed mixture four different deoxyribonucleoside triphosphates and four different chain terminating agents, wherein the DNA polymerase causes production of second, third and fourth series of second, third and fourth DNA products, the number of each second, third and fourth DNA products being approximately the same for substantially all DNA products differing in length from 1 to 20 bases, wherein the number of substantially all the first, all the second, all the third and all the fourth DNA products differing in length from 1 to 20 bases is distinctly different. Most preferably, each second, third and fourth series produce series of second, third and fourth bands, when separated by gel permation according to molecular weight, wherein the intensity of substantially all nearby second series bands, or substantially all nearby third series bands, or substantially all nearby fourth series bands is approximately the same, and wherein the intensity of substantially all nearby bands in a different series is distinctly different; most preferably, the method further includes the steps of determining the position and intensity of each band, the intensity being representative of a particular band series.

In other preferred embodiments, the annealed mixture is provided with a manganese or iron ion, wherein the ion causes the polymerase to be non-discriminatory for a chain terminating agent; the DNA products are separated according to molecular weight in less than four lanes of a gel; the intensity of each band is measured by a gel reading apparatus; the DNA polymerase is chosen from a T7-type DNA polymerase, the large fragment of E. coli DNA polymerase I, and Taq polymerase; and the chain terminating agent is a dideoxynucleoside triphosphate.

In related aspects, the invention features a method for sequencing a strand of DNA, including the steps of either (a) providing a DNA polymerase, and incubating the polymerase and the strand of DNA in a solution including an ion of manganese or iron and a chain terminating agent; or (b) providing a DNA polymerase which is substantially non-discriminating for a chain terminating agent.

In another related aspect, the invention features a method for producing a DNA polymerase for DNA sequencing, including the step of mixing the DNA polymerase in a solution including a manganese or iron ion.

In another aspect, the invention features a solution including a T7-type DNA polymerase, or a Taq polymerase, and a manganese or iron ion. Preferably the ion is at a concentration from 0.005 to 100 millimolar.

In another aspect, the invention features a kit for sequencing DNA having a DNA polymerase, a chain terminating agent, and a manganese or iron ion.

In preferred embodiments, the polymerase is a T7-type DNA polymerase, the large fragment of E. coli DNA polymerase I, or Taq polymerase; the chain terminating agent is a dideoxynucleotide; and the kit further includes a deoxyribonucleoside triphosphate.

In another aspect, the invention features a method for automated sequencing of DNA including providing a polymerase which is substantially non-discriminating for a chain terminating agent and causes production of a series of DNA products differing in molecular weight and terminating with the same chain terminating agent, wherein the DNA products produce substantially all nearby bands of approximately the same intensity.

By substantially non-discriminating is meant that chain terminating agents are incorporated uniformly along the length of the DNA, regardless of the DNA sequence. By approximately the same is meant that the intensity differs by at most two- to three-fold.

In another aspect, the invention features an automated DNA sequencing apparatus having a reactor for providing at least two series of DNA products formed from a single primer and a DNA strand, each DNA product of a series differing in molecular weight and having a chain terminating agent at one end; separating means for separating the DNA products to form a series of bands, the intensity of substantially all nearby bands in a series being approximately the same, and the intensity of substantially all nearby bands in a different series being different, band reading means for determining the position and intensity of each band after separating; and computing means for determining the DNA sequence of the DNA strand directly from the position and intensity of the bands.

In preferred embodiments, the reactor includes a manganese or iron ion, and a T7-type DNA polymerase.

In another aspect, the invention features a solution or kit including a pyrophosphatase, a DNA polymerase, and a chain terminating agent or dITP; and a method for DNA sequencing, including providing pyrophosphatase in the sequencing reaction. Inclusion of pyrophosphatase in a sequencing reaction reduces the level of pyrophosphate and improves the uniformity of band intensity of nearby bands.

In any of the above aspects, the manganese or iron ion may be provided in the presence of a chelate, such as citrate or isocitrate. Such chelates are thought to provide a more controlled level of the desired ion in a DNA sequencing reaction.

In a final aspect, the invention features a T7 DNA polymerase Δ Lys 118—Arg 145, and DNA encoding this polymerase. This polymerase has no detectable exonuclease activity.

We have found conditions under which DNA polymerases can be modified to change their ability to incorporate a chain terminating agent at the elongating terminus of a primer DNA in the presence of a DNA template. This ability allows DNA sequencing to be performed with lower concentrations of chain terminating agents, thus greatly lowering the costs of a DNA sequencing reaction. Further, we have found that DNA polymerases having this ability produce nearby bands in a sequencing gel which are of approximately uniform intensity. That is, the polymerase is no longer discriminating, to any great extent, between incorporating chain terminating agents and normal deoxynucleoside triphosphates. We have shown that at least three polymerases can be modified in this way, including a modified T7 DNA polymerase, the large fragment of E. coli DNA polymerase I, and Taq polymerase. Other polymerases having homology to these polymerases will also work in the invention.

Another advantage of this invention is that the concentration of any given chain terminating agent to be used in a sequencing reaction is readily calculated, since band intensity is directly related to the concentration of any chain terminating agent and is the same for each such agent.

The modified polymerases of this invention are particularly useful in DNA sequencing reactions since only a single sequencing reaction containing all four chain terminating agents at four different concentrations is necessary. Thus, less than four different sequencing reactions can be used for any particular DNA template.

Other features and advantages of the invention will be apparent from the following description of the preferred embodiments thereof, and from the claims.

Description of the Preferred Embodiments

The drawings will first briefly be described.

DRAWINGS

In each of these Figures, the DNA sequenced was mGP1-2 (encoding T7 RNA polymerase, Tabor et al., Proc. Nat. Acad. Sci. USA, 84:4767, 1987), and the primer was the fam primer of Applied Biosystems. In each case the unprocessed (raw) output for the fam primer is shown. The start and end of each output are indicated. In addition, the positions of the sequences are shown, with respect to their corresponding position in wild type T7 DNA. (Dunn et al., J. Mol. Biol. 8:452, 1983) The points on each graph marked by an asterisk represent regions of compression, where at least two DNA products of different molecular weight migrate at the same position on the gel. Compressions are generally described by Tabor et al., Proc. Nat. Acad. Sci. USA, 84 4767, 1987.

Figure 8:
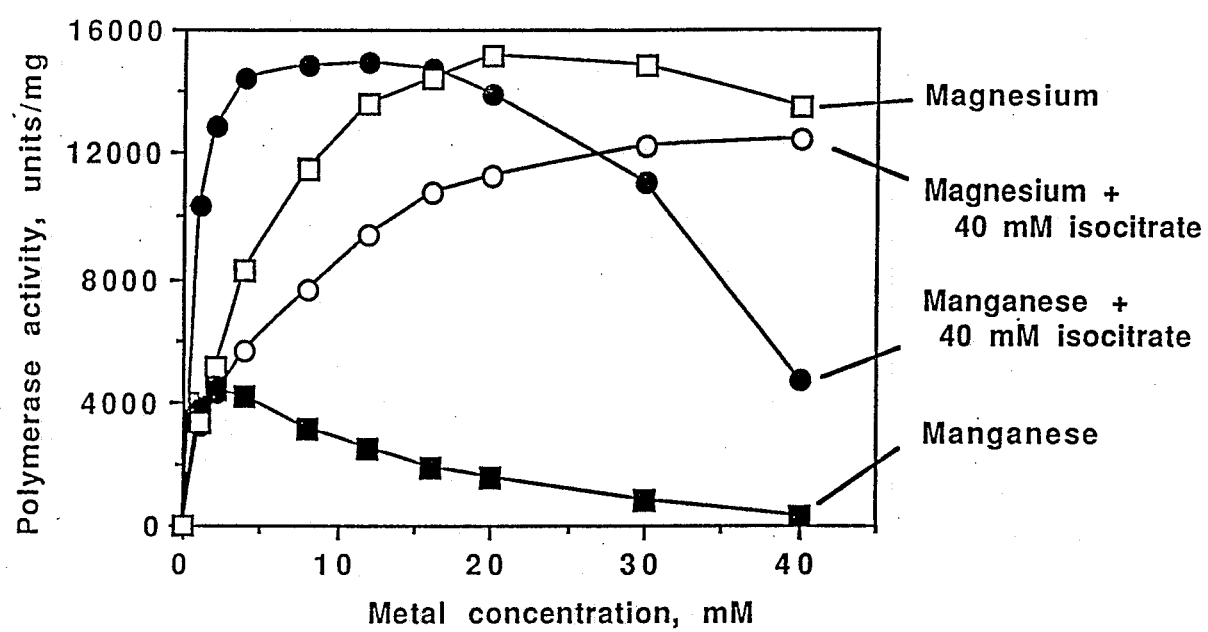

FIG. 8 is a graph showing the optimum concentration of magnesium and manganese for DNA polymerase activity for a genetically modified T7 DNA polymerase in the presence and absence of 4.0 mM isocitrate.

Figure 9:
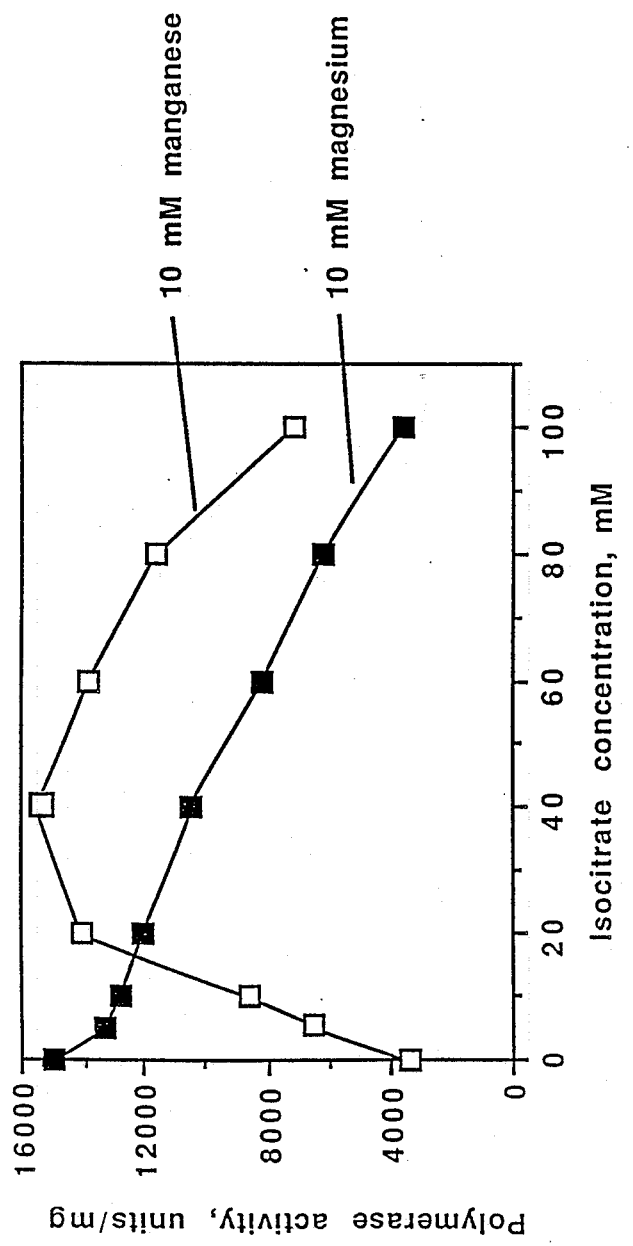

FIG. 9 is a graph showing the effect of different concentrations of isocitrate in the presence of 10 mM magnesium or manganese on DNA polymerase activity for a genetically modified T7 DNA polymerase.

Figure 10:
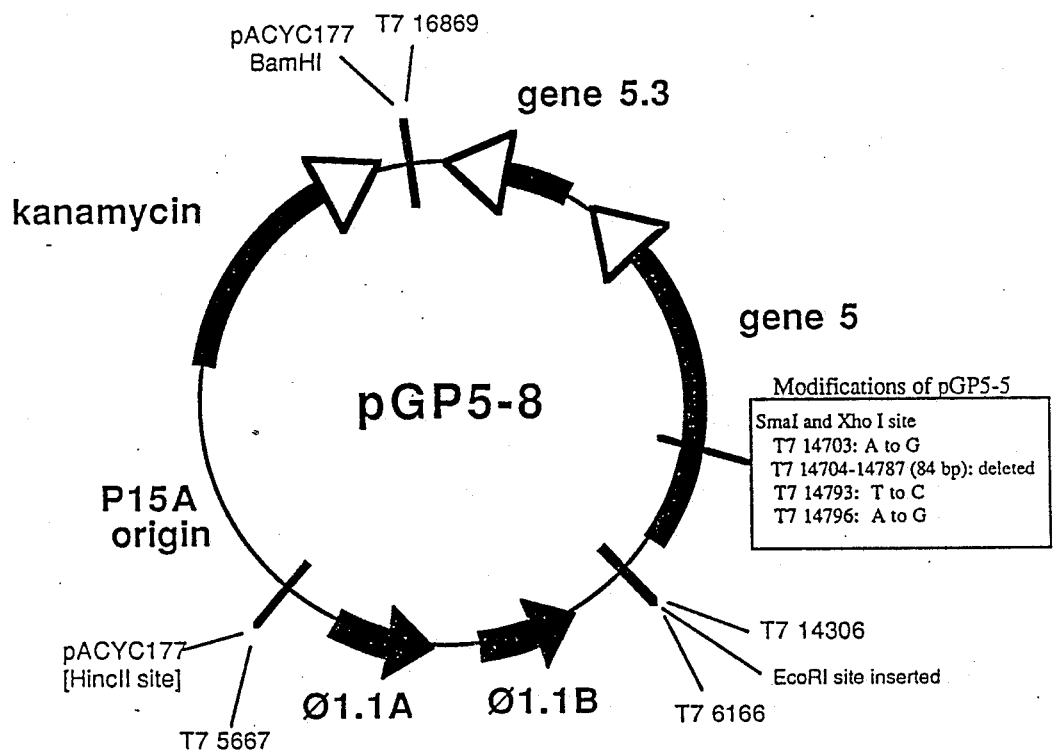

FIG. 10 is a schematic map of pGP5 8, a plasmid that encodes for a genetically modified T7 DNA polymerase lacking amino acids Lys 118 through Arg 145, that lacks exonuclease activity.

Figure 11:
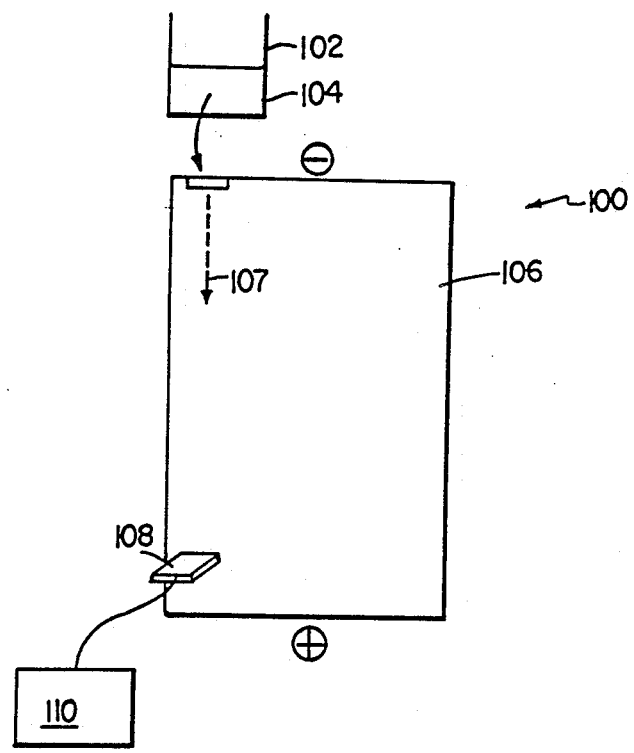

FIG. 11 is a diagrammatic representation of an automatic sequencing apparatus of this invention.

DNA Polymerase

DNA polymerases useful in this invention include those belonging to a class of homologous polymerases including T7 type DNA polymerases (such as T7, T3, ΦI, ΦII, H, W31, gh-1, Y, All22, or SP6), the large fragment of E. coli DNA polymerase I and Taq polymerase. By homologous polymerases is meant an enzyme that discriminates against dideoxynucleoside triphosphates compared to deoxynucleoside triphosphates in the presence of magnesium; however, when magnesium is replaced by manganese the discrimination against dideoxynucleoside triphosphates is reduced. These polymerases are used in a DNA sequencing reaction under conditions in which they produce nearby bands of approximately uniform intensity (with about a 1.5- to 2.0-fold variation in intensity) when the DNA products of the sequencing reaction are run in a gel. By nearby is meant to include bands representing DNA products of molecular weight differing by as much as 6000, i.e., 20 bases. The actual value of this intensity will decrease along the length of the gel, as described below and shown in the Figures. Band intensity reflects the number of DNA products within a certain band. Labels, such as fluorophores or radioisotopes, are used to produce a readily detectable band of intensity reflective of the number of such DNA products. Thus, in this invention, nearby bands derived from one sequencing reaction with one chain terminating agent have approximately the same number of DNA products and thus a uniform band intensity. The sequencing conditions include incubation of the polymerase in the presence of specific divalent or trivalent cations such as manganese (II and III), ferrous and ferric ions; monovalent and divalent cations which have no detectable effect, or are detrimental to DNA synthesis, include: K, Na, Ba, Be, Ca, Ce, Cr, Co, Cu, Ni, Si and Zn. The anion is unimportant, for example, chloride, acetate, and sulfate are suitable. Under these conditions the requirement for chain terminating agents, such as dideoxynucleosides, is lessened by almost 1000-fold for enzymes such as large fragment of E. coli DNA polymerase I and Taq polymerase, and by about 10-fold for a modified T7 polymerase. A chelator may also be provided in this solution in order to help regulate the concentration of available divalent metal ions. For example, citrate or isocitrate may be provided. These chelates are thought to maintain the level of, for example, free manganese ions at a concentration of between 10 and 100 μM over a wide range of manganese concentrations. That is, the chelator acts as a buffer.

The DNA polymerases of this invention do not discriminate significantly between dideoxynucleoside analogs and deoxynucleosides along the length of the DNA template. That is, in the presence of manganese or iron these polymerases are unable to discriminate between a nucleotide that has a 3' hydroxyl group versus one that does not (i.e., has two hydrogens at the 3' position of the ribose). However, these polymerases do discriminate against modifications at other positions on the nucleosides, even in the presence of manganese or iron. For example, the polymerases do discriminate against some dideoxynucleoside analogs which have fluorescent groups attached compared to deoxynucleosides. However, the polymerase do not discriminate to a different extent at neighboring, or nearby nucleotides, on the basis of the presence or absence of the modification to the dideoxynucleoside. Thus, while they discriminate strongly against these analogs, requiring higher concentrations for a DNA sequencing reaction compared to unmodified dideoxynucleosides, the intensity of nearby bands will still be uniform. For example, there is a 10 fold discrimination against dideoxy ITP (ddITP), compared to dideoxy GTP (ddGTP), in the presence of Mn However, all the bands produced in a sequencing reaction are of equal intensity with ddITP since there is no differential discrimination along the length of the DNA template.

Thus, the polymerases of this invention provide a uniform efficiency of incorporation of chain terminating agents, even if they discriminate against overall incorporation.

Chain terminating agents useful in this invention include dideoxynucleosides having a 2', 3' dideoxy structure. Other agents useful in the invention are those able to specifically terminate a DNA sequencing reaction at a specific base, and are not discriminated against by the polymerase under the above conditions.

In order to determine whether any particular DNA polymerase, in combination with any particular chain terminating agent, or other component of a sequencing reaction mixture, is useful in this invention, a standard sequencing reaction is performed, as described below and shown in the drawings, and the extent of band formation, and the uniformity of nearby bands in a sequencing gel, reviewed. If the polymerase reaction does not extend the primer by at least 20 bases, it is not suitable under the conditions used. Adjacent band uniformity within a two-fold or less range is useful in this invention, preferably the uniformity is within a 1.0–1.5 fold range. Similarly, determination of optimum cation concentration, or of other potential cations useful in the invention, is determined by use of this sequencing reaction under various conditions. For example, cations are tested in ranges from 0.005–100 mM. An example of such an experiment follows:

DNA synthesis is measured using a 17-mer primer of sequence 5'-GTAAAACGACGGCCAGT-3' (New England Biolabs catalog number 1211) that has been labeled with $^{32}$P at its 5' end and annealed to single-stranded mGP1-2 DNA. Tabor et al., proc. Nat. Acad. Sci. USA 84:4767 (1987) and Tabor et al., J. Biol. Chem. 262:16212 (1987). Any other template is equally useful in this reaction. This primer-template is used in a reaction that contains a DNA polymerase in the presence of a range of concentrations of a metal ion. Reactions are carried out in the presence of a given concentration of all 4 deoxynucleotides (dNTPS, 20–200 μM), and over a range of concentrations of one dideoxynucleotide (ddNTP, in this example, ddGTP from 10–500 μM). The DNA products are then analyzed by polyacrylamide gel electrophoresis, where DNA synthesis is detected as extensions of the primer producing bands, representing extensions of various molecular weights, in the gel.

In a specific example, each reaction mixture (10μl) contained 0.1 μg$^{32}$P-primer-template, 40 mM Tris-HCl pH 7.5, 5 mM dithiothreitol (DTT) 5μM to 20mM metal ion, 10 to 500 μM 4dNTPs, 1 to 500 μM ddNTPs, and 2 units of a DNA polymerase. Incubation was at 37° C. for 15 min. The reaction was stopped by addition of 10μl of 90% formamide, 50 mM EDTA, and 0.1% bromophenol blue.

The resulting samples were heated at 75° C. for two minutes immediately prior to loading onto a polyacrylamide gel (8% acrylamide, 0.3% bisacrylamide) in 7M urea, 100 mM Tris-borate, pH 8.9. Electrophoresis was at 2000 volts for 2 hours. The gel was fixed in 50% methanol, 10% acetic acid for 30 min., dried, and exposed, for autoradiography. Band intensity in each lane of the resulting film was determined by scanning each lane with a densitometer. The densitometer used was a double-beam recording instrument, model MkIIIC (Joyce, Loebl & Co., Ltd., Gateshead-on-tyne, II, England). Any suitable densitometer instrument for scanning gels will also work. Alternatively, the uniformity of the resulting bands can be determined by scanning the DNA products as they are electrophoresed within the gel.

The ability to incorporate a given ddNTP compared to the corresponding dNTP for any one enzyme is measured as the ratio of ddNTP to dNTP necessary to allow DNA synthesis that terminates in a fixed range, detected as producing bands of no greater than a fixed molecular weight. That is, the bands produced in the reaction end within a specified range in the sequencing gel. Thus, if one enzyme discriminates 1000-fold greater against a given ddNTP compared to another enzyme, a 1000-fold higher ratio of ddNTP to dNTP will be necessary to obtain bands terminating at the corresponding sites in the same range of the gel.

Manganese (Mn)

Following is a series of examples of the use of a modified T7 DNA polymerase or the large fragment of *E. coli* DNA polymerase I in DNA sequencing reactions with Mn present in the sequencing buffer. These examples are not limiting to this invention and are given simply to provide those skilled in the art with guidelines for use of DNA polymerases of this invention. As described above, those skilled in the art can readily determine other conditions under which DNA polymerases of this invention can be produced that will give the properties described here with respect to uniformity of chain terminating agent incorporation and use in a sequencing reaction.

The specific modified T7 DNA polymerase used in the following examples was genetically modified to have no detectable exonuclease activity. This genetically modified DNA polymerase is termed ΔLys 118-Arg 145 (Δ28) since the amino acid region from Lys 118 through Arg 145 in T7 DNA polymerase is deleted. The gene encoding this polymerase was constructed in a plasmid pGP5-8 as a variant of the plasmid pGP5-5 as stated in our copending application Ser. No. 132,569, was deposited with the ATCC on Jan. 13, 1987 and assigned No. 67,287. The specific mutation to pGP5-8 was carried out by the same procedure as described for other mutations in said copending application, that is, by first cloning the T7 gene 5 from pGP5-3 (Tabor et al., J. Biol. Chem. 282, 1987) into the SmaI and HindIII sites of the vector M13 mp18, to give mGP5-2. (The vector used and the source of gene 5 are not critical in this procedure.) Single-stranded nGP5-2 DNA was prepared from a strain that incorporates deoxyuracil in place of deoxythymidine (Kunkel, Proc. Natl. Acad. Sci. USA 82, 488, 1985). This procedure provides a strong selection for survival of only the synthesized strand (that containing the mutation) when transfected into wild-type *E. Coli*, since the strand containing uracil will be preferentially degraded. Mutant oligonucleotides, 15–20 bases in length, were synthesized by standard procedures. Each oligonucleotide was annealed to the template, extended using native T7 DNa polymerase, and ligated using T4 DNA ligase. Convalently closed circular molecules were isolated by agarose gel electrophoresis, run in the presence of 0.5μg/ml ethidium bromide. The resulting purified molecules were then used to transform *E. coli* 71.18. DNA from the resulting plagues was isolated and the relevant region sequenced to confirm each mutation.

Referring to FIG. 10, pGP5-8 includes pACYC177 resected at BamHI and HincII sites, T7 DNA from bases 5667 to 6166 containing Φ1.1A and Φ1.1B, and T7 DNA bases 14,306 to 16,869 containing gene 5 with modifications shown in FIG. 10. pGP5-8 was constructed by first synthesizing the 34 mer, 5'CCGGCAAGTTGCCCGGGATGCTCGAG-GAGCAGGG 3'. This oligonucleotide was used as a primer for DNA synthesis on the single-stranded DNA of M13 mGP5-2, that contains an insert that encodes T7 gene 5, DNA synthesis and mutant selection was performed as described above. After construction of the desired mutation in-m-GP5-2, the appropriate region of T7 gene 5 that contains the 84 bp deletion was inserted into pGP5-5 by isolating an EcoRI to HpaI fragment containing T7 DNA from positions 14,306 to 15,610, including the region including the 84 bp deletion, and ligating it into the comparable region of pGP5-5. The derivative pGP5-8 was confirmed to contain the deletion by the presence of the SmaI and XhoI sites that are created by the mutagenesis, and by DNA sequence analysis of the region containing the 84 bp deletion pGP5-8 was transformed into the strain K38/pTrx-3, to create the strain K38/pTrx-3/pGP5-8. Induction of K38/pTrx-3/pGP5-8, and purification of the genetically altered T7 DNA polymerase, was carried out using the same procedure as that described for the analogous strain K38/pTrx-3/pGP5-5 in application Ser. No. 132,569, namely, by infection of the mutant phage into K38/pGP1-2, as follows. The cells were grown at 30° C. to an $A_{590}=1.0$. The temperature was shifted to 42° C. for 30 min., to induce T7 RNA polymerase. IPTG was added to 0.5 mM, and a lysate of each phage was added to a moi=10. Infected cells were grown at 37° C. for 90 min. The cells were then harvested and extracts prepared by standard procedures for T7 gene 5 protein.

Extracts were partially purified by passage over a phosphocellulose and DEAE A-50 column, and assayed by measuring the polymerase and exonuclease activities directly, as described above. Since this polymerase has no detectable exonuclease activity chemical modification, as described by Tabor et al., Id., is not necessary before its use in a DNA sequencing reaction. The genetically modified T7 DNA polymerase used in the examples below was a preparation with an activity of 1000 units/ml.

EXAMPLE 1

DNA sequencing Reaction Using Manganese

Standard DNA sequencing reaction methodology is used for sequencing DNA in the presence of Mn. For T7 DNA polymerase the general sequencing steps are described in detail in Tabor et al., Id. Briefly, the steps and conditions are as follows:

A. Annealing Reaction

In the annealing reaction the following solution was prepared:

| | |
|---|---|
| DNA to be sequenced (e.g., mGPL1-2 DNA) | 7 μl |
| in 10 mM Tris-HCl pH 7.5, 0.1 mM EDTA, 2 μg/7 μl | 2 |
| 5X SeqBuf (200 mM Tris-HCl pH 7.5, 5 mM MnCl₂, 250 mM NaCl) | |
| Primer (New England Biolabs-17mer, Cat #1210 | 1 |
| 0.5 pm/μl) | |
| | 10 μl |

This solution was heated at 65° C. 2 min, and slow cooled to room temperature.

B. Labeling reaction

In the labeling reaction the following solution was prepared:

| | |
|---|---|
| Annealing reaction mixture | 10 μl |
| Dithiothreitol 0.1M | 1 |
| [³⁵S]dATP, New England Nuclear NEG-034H | 1 |
| dTTP, dCTP, dGTP 1.5 μM each | 2 |
| Genetically mmodified T7 DNA polymerase, 1 unit/μl | 2 |
| (ΔLys118-Arg 145, as described above) | 16 μl |

This was incubated at room temperature for 5 min.

C. Termination Reaction

In the termination reactions, four reaction mixtures were prepared as follows:

| | G | A | T | C |
|---|---|---|---|---|
| 5X SeqBuf | 0.6 | 0.6 | 0.6 | 0.6 μl |
| 4dNTPs (3 mM) | 0.3 | 0.3 | 0.3 | 0.3 μl |
| H₂O | 1.9 | 1.9 | 1.9 | 1.9 μl |
| ddGTP 0.2 mM (dd=dideoxy) | 0.2 μl | | | |
| ddATP 0.2 mM | | 0.2 μl | | |
| ddTTP 0.2 mM | | | 0.2 μl | |
| ddCTP 0.2 mM | | | | 0.2 ml |
| | 3 | 3 | 3 | 3 μl |

The termination mixtures were incubated at 37° C. for 2 min, and then 3 μl aliquots of the completed labeling reaction added to each termination mixture. The resulting solution was incubated at 37° C. for 5 min.

The termination reactions were stopped with 5 μl of 90% formamide, 20 mM EDTA, 0.2% bromophenol-blue, xylene-cyanol, pH 8.0. The resulting samples were heated at 75° C. for two minutes, loaded onto a polyacrylamide gel (8% acrylamide, 0.3% bisacrylamide) in 7M urea, 100 mM Tris borate pH 8.9, and electrophoresed at 2000 volts for 2 hours. The gel was fixed in 50% methanol, 10% acetic acid for 30 min, dried and used to expose film by autoradiography.

The exposed gel was developed, and the intensity of radioactive bands in each lane was determined by scanning each lane with a densitometer (Joyce, Loebl & Co., Ltd., model number MkIIIC).

When the same sample is run in the presence of magnesium in place of manganese, the underlined bases in the following triplets are 2–5 fold more intense than adjacent bases whenever these triplets appear: TCT, AAG, GCA, CCT. However, in the example just described, bands corresponding to every base in all the triplets just shown have the same intensity, differing by at most 20% from one another.

EXAMPLE 2

Sequencing reaction using manganese, 2X ddGTP and 1X ddCTP to differentiate between G and C by relative band intensities.

In this example, only one vessel was used to perform a sequencing reaction to determine the sequence of two types of bases (namely C and G) in a DNA template. The steps were as follows:

In the annealing reaction the following solution was prepared:

| | |
|---|---|
| mGPL-2 DNA (2.7 mM in 10 mM Tris-HCl pH 7.5, 0.1 mM EDTA) | 8.6 μl |
| 5X SeqBuf | 4 |
| Primer (ABI fam primer, 0.4 pm/μl) | 2 |
| H$_2$O | 5.4 |
| | 20 μl |

This solution was heated at 65° C. 2 min, and slow cooled to room temperature. The fam primer is labelled with a fluorescent label which can be detected as it passes through a sequencing gel, using the ABI Model 370 A DNA Sequencing System.

In the extension reaction the following solution was prepared.

| | |
|---|---|
| Annealing reaction mixture | 20 μl |
| Dithiothreitol 0.1M | 1 |
| 4 dNTP 3 mM | 3 |
| ddGTP 30 μM | 3 |
| ddCTP 30 μM | 1.5 |
| | 28.5 μl |

This solution was incubated at 37° C. for 2 min, 1.5 μl of genetically modified T7 DNA polymerase (Δ28), 1 unit/μl, added, and the solution incubated at 37° C., for 10 min. The reaction was stopped by adding 5 μl of 100 mM EDTA, pH 8.0.

The resulting fragments were precipitated as follows: 3.5 μl 3M sodium acetate, and 100 μl 100% ethanol was added. After incubation on ice for 10 min, the mixture was centrifuged for 30 min at 4° C. in a microcentrifuge. The pellet was washed with 500 μl 70% ethanol, and centrifuged again for 5 min. The supernatant was decanted, and the pellet dried by centrifuging under vacuum for several minutes. The sample was then resuspended in 5 μl 90% formamide, 50 mM EDTA pH 8.0, heated at 75° C. for two minutes, and loaded onto an ABI Model 370A DNA Sequencing System. The instrument was run and the unprocessed (raw) data was collected as described in the User's Manual for the model 370A instrument (Preliminary version, Mar. 1987, Sections 3, 4 and 5). Unprocessed (raw) output for only the fam primer is shown.

Figure 4:
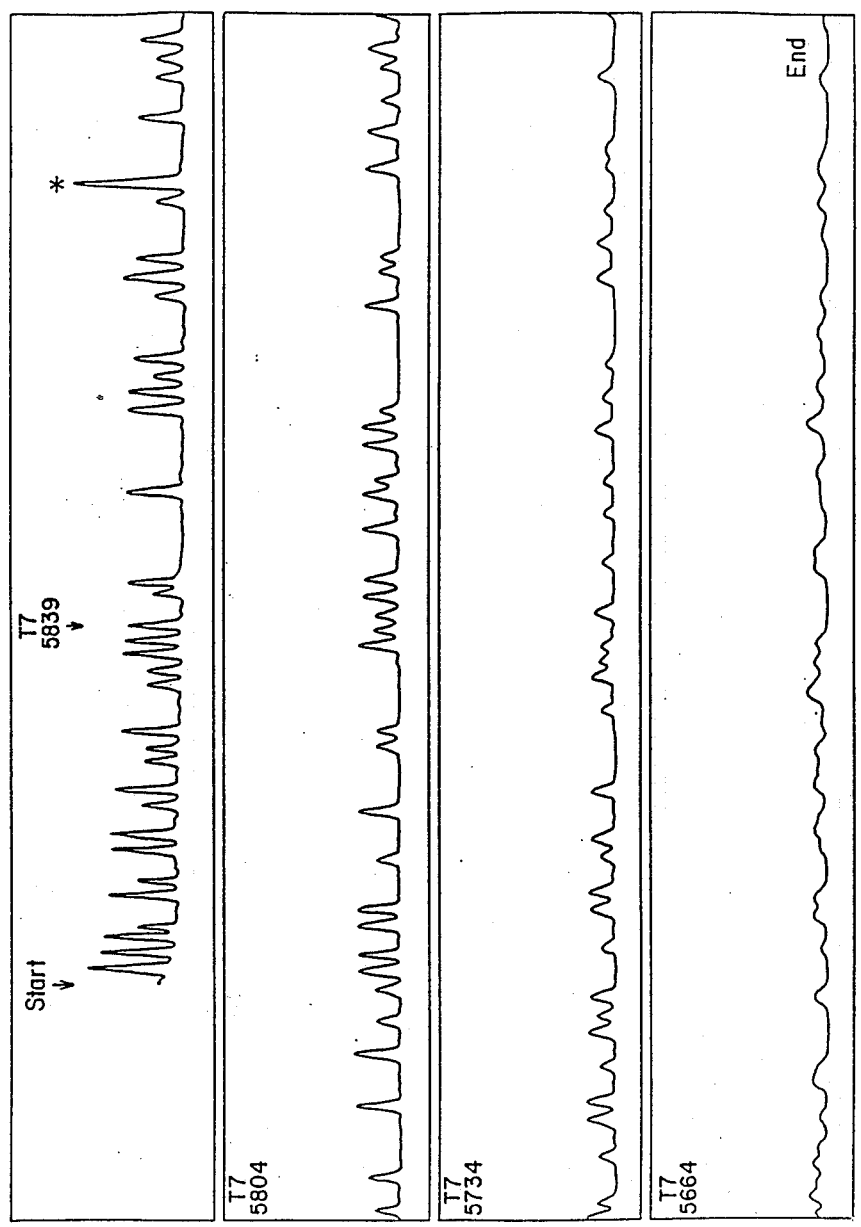

The output from this reaction is shown in FIG. 4. Each G is represented by a tall peak and each C by a short one. Thus, the sequence of G's and C's in the DNA is determinable from the peak height. Thus, from one sequencing reaction, with only one label used for all DNA products, a DNA sequence of G's and C's can be determined. Peak height becomes reduced along the length of a gel since products of higher molecular weight are present in lower amounts. However, the difference between a nearby G and C remains about 2 fold along the gel, while that of a pair of nearby G's or a pair of nearby C's is approximately uniform (varying about 1.1- to 1.4-fold), correcting for the decrease in intensity for each additional position along the sequence. For example, in FIG. 4 the signal decreases 2 fold for a given series of bands over a period of approximately 60 bases. Thus there is a 1.16% decrease inherent at each additional position along the template in this example (since Chi is 1.0116 for Chi$^{60}$=2).

It is important to distinguish between bands of different intensity due to different efficiency of chain termination within nearby bands, and two or more bands migrating together during electrophoresis. The latter event, called a compression, is an artifact of gel electrophoresis, and not the DNA sequencing reaction itself, and is not eliminated by using manganese. One example of such a compression is marked by an asterisk (*) in FIG. 4. If one knows that such a compression represents the co-migration of two DNA products, as the one noted in FIG. 4, then that band is an accurate marker of a band of 2X intensity.

The precise sequence in a region of compression cannot be determined. In order to determine this sequence, it is necessary either (1) to determine the sequence in the reverse orientation, (2) run the sequencing gel under stronger denaturing conditions, i.e., higher temperature, or by the addition of 50% formamide, or (3) use a nucleotide analog, e.g., dITP or deazaGTP, in place of dGTP. Compressions are due to the formation of stable hairpins in the DNA under the conditions of gel electrophoresis; incorporation of these nucleotide analogs destabilize most of these hairpins.

Compressions due to hairpin structures can be of virtually any length, depending on the extent and strength of the hairpin. Thus, with Mn all nearby bands have an approximately equal numbers of DNA products of the same molecular weight, but do not necessarily have a similar band intensity due to compressions.

Figure 1:
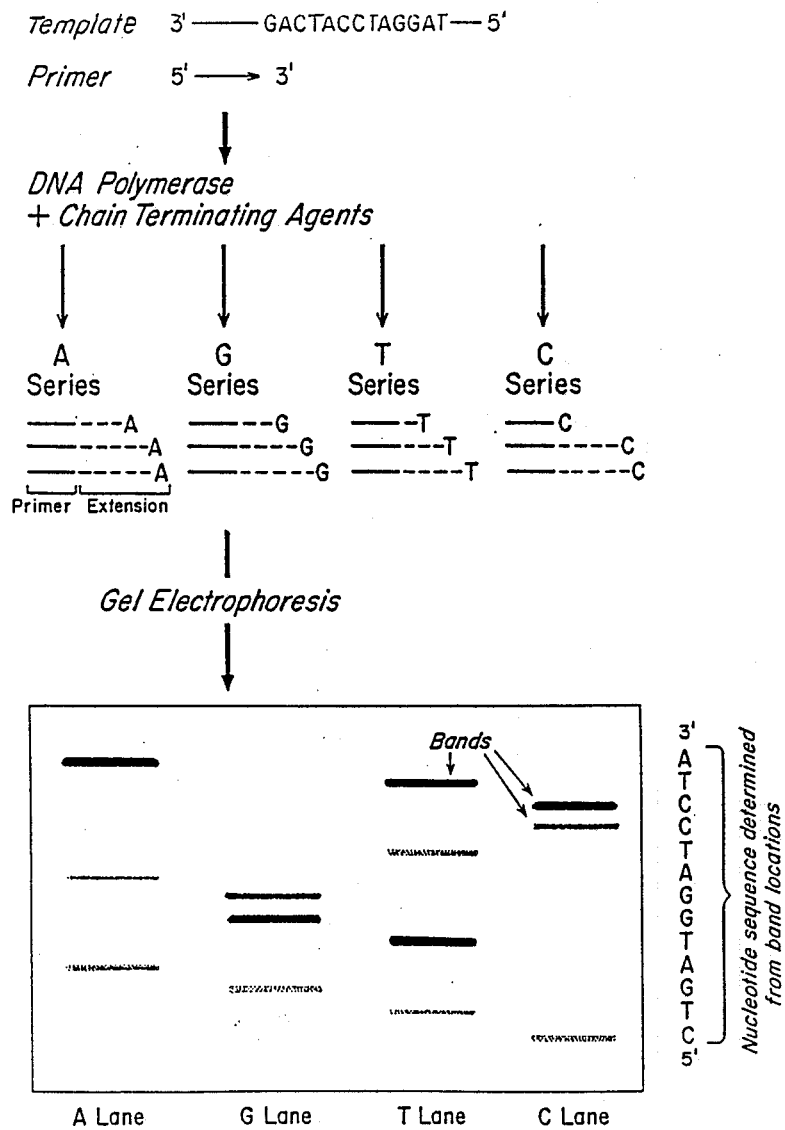
FIG. 1 is a schematic representation of DNA sequencing by the method of Sanger et al., supra.
Figure 2:
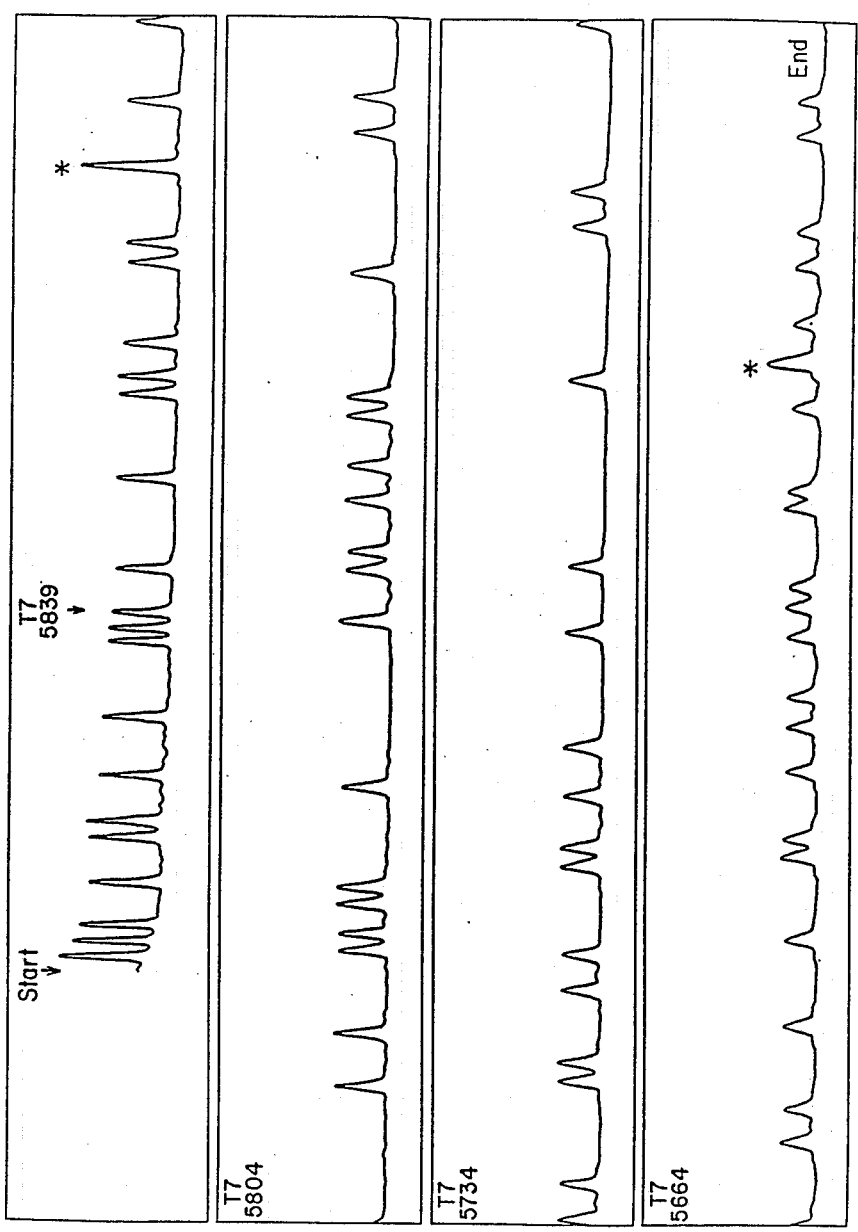
FIGS. 2-7 are graphical representations of relative band intensities of six different sequencing gels scanned by an Applied Biosystems Model 370A DNA Sequencing System, each from a single gel lane containing a sequencing reaction mixture resulting from using a genetically modified T7 DNA polymerase in the presence of various mixtures of manganese or magnesium and various dideoxynucleosides.

Referring to FIG. 2, the above method was used with just ddGTP in the presence of manganese at a 1 mM final concentration. Each band on the resulting gel is represented in FIG. 2 as a peak. The intensity of a band is reflected by the height of each peak. With manganese, nearby band intensity and thus peak height is approximately uniform along the gel, differing between nearby bands by less than 5 or 10%.

Figure 3:
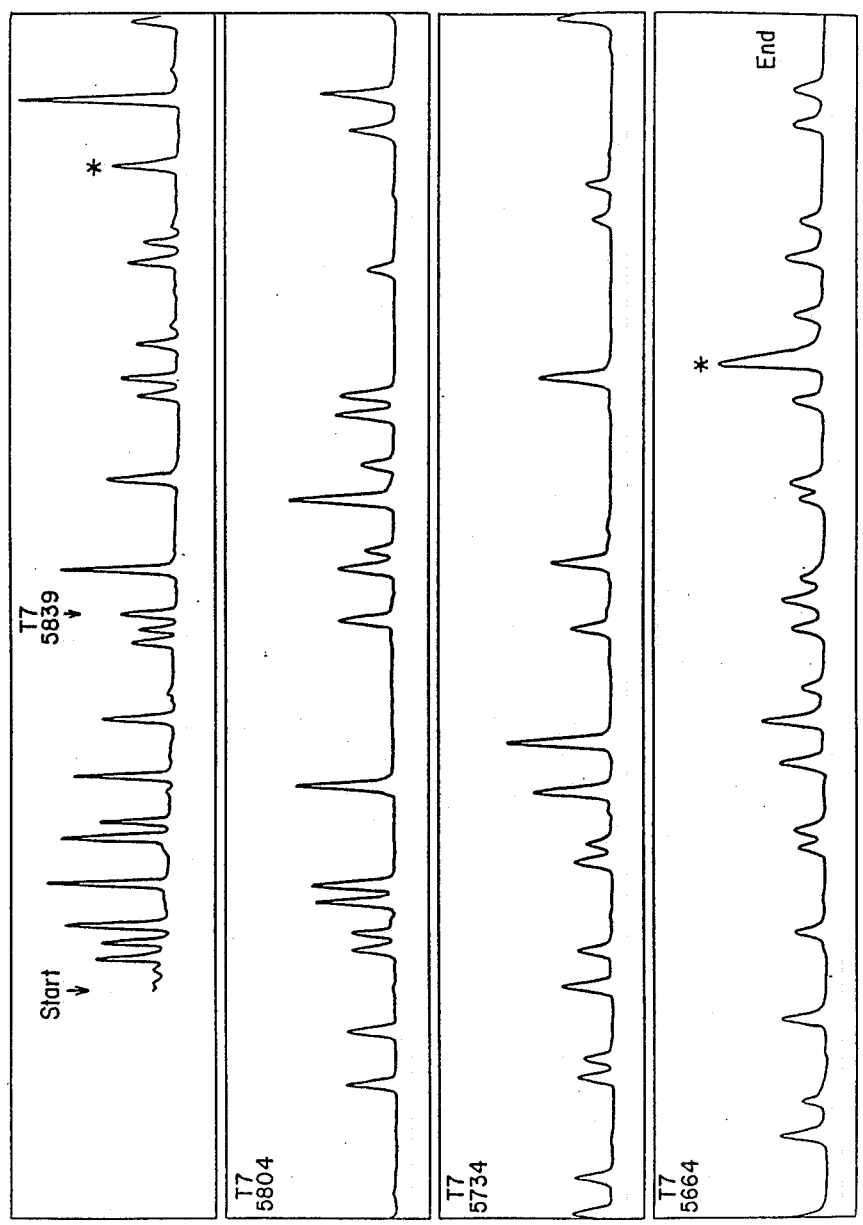

In contrast, the output shown in FIG. 3 represents the same experiment run in the presence of magnesium instead of manganese. Here, nearby band intensity and thus peak height varies as much as 10 fold.

Figure 5:
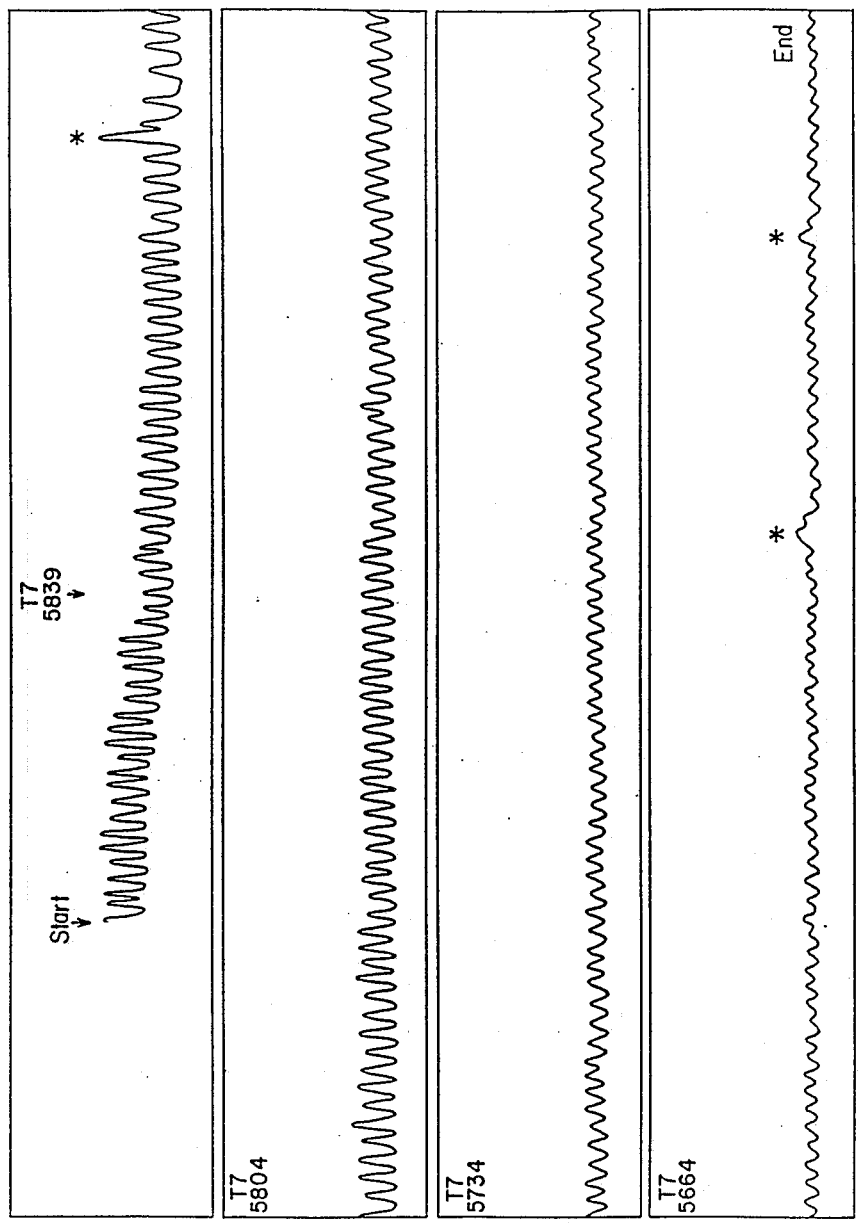
Figure 6:
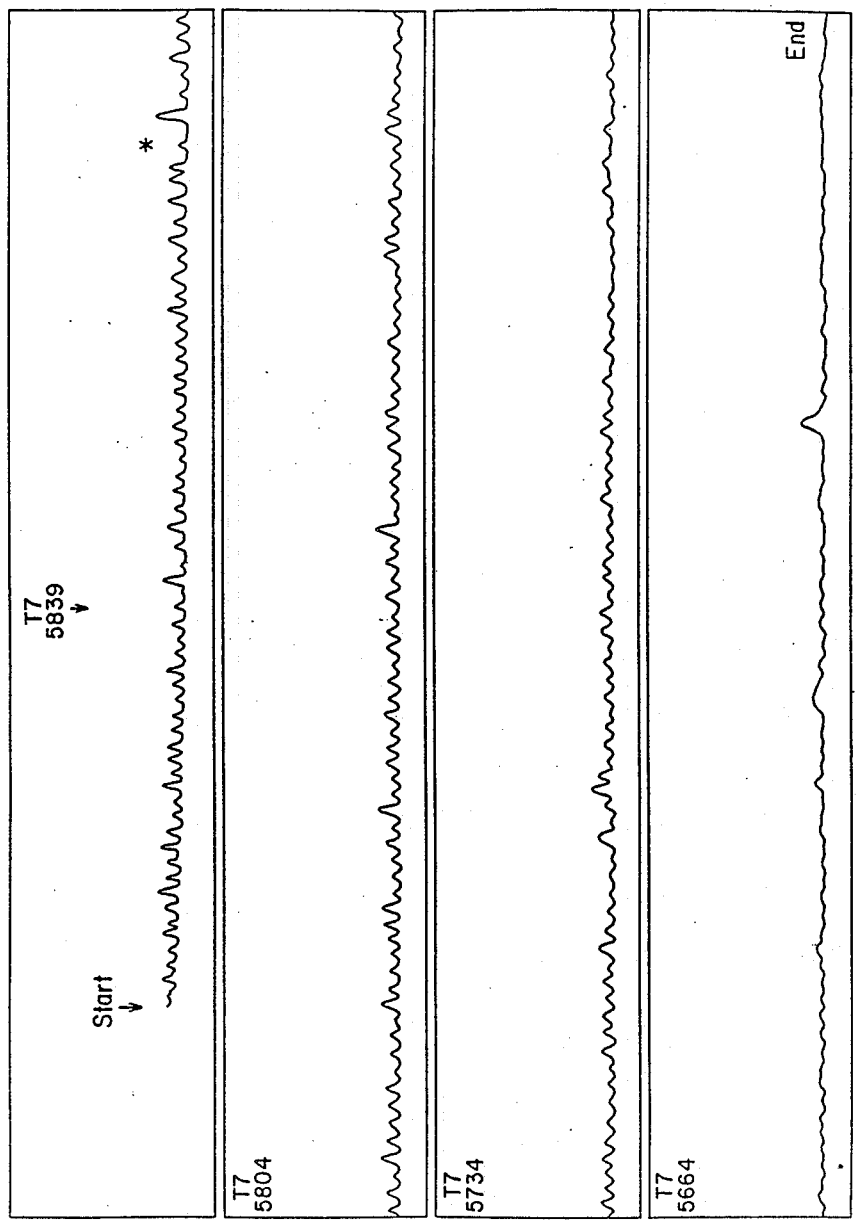

Referring to FIG. 5, with all four dideoxy nucleotides at equal concentrations (0.75 μM final concentration for each ddNTP, as in Example 2) in a sequencing reaction in the presence of manganese, nearby bands and corresponding peaks are approximately uniform, varying by no more than about 1.5-fold again decreasing in absolute intensity for DNA products of higher molecular weight. In contrast, in the presence of magnesium and all four dideoxy nucleotides at equal concentration, as shown in FIG. 6, nearby band intensity varies greatly.

Figure 7:
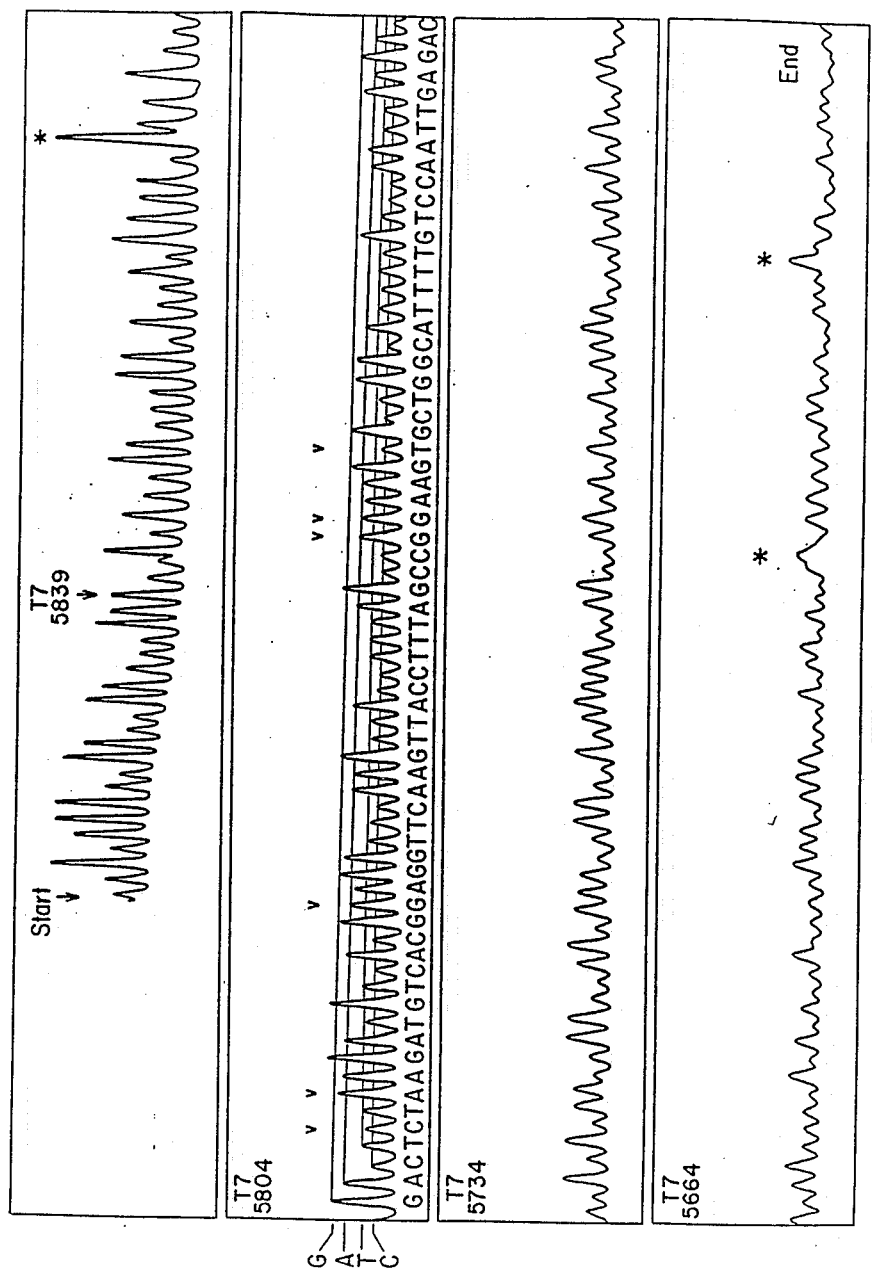

By varying the concentration of each ddNTP in a sequencing reaction the complete nucleotide sequence of a strand of DNA can be determined. An example of such a procedure is shown in FIG. 7, where the concentration of each ddNTP differs by 30% intervals: ddGTP (4.5 μM 2.2x), ddATP (3.0 μM, 1.7x), ddTTP (2 μM, 1.3x) and ddCTP (1.4 μM, 1.0x). The DNA sequence determined from this graph is shown below the second line in the Figure. Only 6 mistakes (shown by a v) were made compared to the actual DNA sequence. These mistakes can be eliminated by using greater ratios of each ddNTP (e.g., 1xddCTP, 2xddTTP, 4xddATP and 8xddGTP). Similarly, by measuring peak areas, rather than peak height, the results are more accurate. Computer programs to measure such peak areas are readily written for existing DNA sequencing machines.

Referring to FIG. 8, the optimum concentration of manganese in a sequencing reaction is 1 mM, in the absence of a chelator such as citrate or isocitrate, compared to 20 mM for magnesium. When 40 mM isocitrate is present in the reaction, the polymerase activity in the presence of manganese is stimulated 4-fold, and the optimum manganese concentration is 5 to 20 mM. Referring to FIG. 9, at 10 mM manganese concentration, the optimal isocitrate concentration is 40 mM, resulting in a 4-fold stimulation of polymerase activity. At 10 mM magnesium concentration, any amount of isocitrate has an inhibitory effect on polymerase. These results were obtained by performing polymerase reactions, as described below, in the presence of various chelator and ion concentrations. Specifically, reactions (200 $\mu l$) contained 40 mM Tris-HCl, pH7.5, 5 mM dithiothreitol, 0.5 mM denatured calf thymus DNA, 0.3 mM dGTP, dATP, dCTP and [$^3$H]dTTP (20 cpm/pm), 50 ug/ml BSA, and the indicated concentrations of $MgCl_2$, $MnCl_2$ or sodium isocitrate. Reactions were begun by the addition of 0.1 unit of genetically modified T7 DNA polymerase ($\Delta$Lys118-Arg145). Incubation was 37° C. for 30 min. Reactions were stopped by the addition of 3 ml of 1N HCl and 0.1 M sodium pyrophosphate, and the acid insoluble radioactivity was determined. One unit of DNA polymerase catalyzes the incorporation of 10 nmoles of total nucleotide into an acid insoluble form in 30 min. under the conditions of the assay. (Tabor et al. J. Biol Chem. 262; 16212, (1987)).

Pyrophosphatase

When chemically modified T7 DNA polymerase is used for DNA sequencing, specific fragments disappear upon prolonged incubation (Tabor and Richardson, Proc. Nat. Acad. Sci. USA 84:4767, 1987). We refer to the sites where this occurs as "holes" since this process creates a space in the sequencing gel. The holes occur more frequently when dITP is used in place of dGTP.

The degradation of specific fragments is an obvious problem in reading DNA sequencing gels. The absence of a fragment is either missed completely when the sequence is read, resulting in a deletion in the determined sequence, or else a hole is observed that can only be interpreted as an unknown base at that position.

The current solution to this problem is to keep the reaction times short. This is unsatisfactory for two reasons. First, it makes running the reactions technically more difficult, since one is forced to work very rapidly in order to terminate the reactions soon after they are begun. More importantly, some bands are extremely sensitive to this degradation, and disappear even after very short reactions times.

We have constructed a genetically altered form of T7 DNA polymerase ($\Delta$28, described above) that has no detectable level of exonuclease activity ($<10^{-7}$ the level of the wild type enzyme, or $>10,000$ times lower than the chemically modified T7 DNA polymerase). We expected that, since the holes appear with prolonged incubation, they were presumably due to exonuclease activity, and thus would not occur when this genetically modified form of T7 DNA polymerase was used. However, the radioactive fragments mentioned above still disappear at the same rate when either chemically or genetically modified T7 DNA polymerase is used.

We have determined that this loss of specific bands is due to pyrophosphorolysis activity of the polymerase. This activity is not due to the exonuclease activity of DNA polymerase, but rather to the reversal of the polymerase activity: in the presence of pyrophosphate (PPi), the polymerase will add PPi to the terminal nucleotide that is located at the 3 terminus of the chain, in this case releasing a dideoxynucleoside 5 triphosphate. See generally Deutscher et al. J. Biol. Chem. 244:3019, 1969; and Kornberg, DNA Replication pp. 125-126, published by Freeman & Co., SF. This reaction has the effect of removing the block at the 3' terminus, permitting synthesis to extend further along the template. PPi normally accumulates in a DNA synthesis reaction mixture, since it is a product of the polymerization reaction. The site of pyrophosphorolysis is DNA sequence dependent, and thus the holes described above are produced only at specific sites.

To overcome this problem, the pyrophosphorolysis reaction must be inhibited. One way to inhibit pyrophosphorolysis is to break down the pyrophosphate as it is generated in the polymerase reaction, by adding the enzyme pyrophosphatase. Other solutions include altering the pyrophosphate by other enzymatic reactions, or preventing the pyrophosphorolysis reaction by the addition of an analog that inhibits this activity of the DNA polymerase. We have found that the addition of even trace amounts of this enzyme (one thousandth the molar ratio of DNA polymerase molecules) to the sequencing reactions completely stabilizes the specific class of fragments mentioned above and eliminates production of holes. In the presence of both the genetically altered form of T7 DNA polymerase ($\Delta$28) and pyrophosphatase, all bands are stable upon even prolonged incubation (up to 2 hours).

For automated sequencing, using differential band intensity, it is critical that the intensity of every band is determined entirely by the ratio of ddNTP to dNTP. Pyrophosphorolysis will create ambiguities by diminishing the intensity of some bands. Thus, addition of pyrophosphatase is particularly useful in this sequencing procedure.

Pyrophosphatase should be added whenever chemically or genetically modified T7 DNA polymerase or other polymerases are used for sequencing, at at least an amount sufficient to catalyze the hydrolysis of the PPi formed at a rate that will prevent the accumulation of PPi to a level that will lead to pyrophosphorolysis. This is particularly true when dITP is used in place of dGTP, in which case the appearance of holes due to pyrophosphorolysis reaction occurs to a greater extent.

EXAMPLE 3

Protocol using pyrophosphatase in sequencing reactions

In this example, a normal sequencing protocol was followed. The only modification was that yeast inorganic pyrophosphatase was used. The source of the pyrophosatase is not important, however in this example we used Sigma yeast inorganic pyrophosphatase catalog number I-4503, without further purification, or further purified on an FPLC mono Q column, and Worthington yeast inorganic pyrophosphatase without further purification. The pyrophosphatase was added to modified T7 DNA polymerase prior to adding the polymerase to the labeling reaction. Typically, 2 units (0.25 µg) of polymerase were used per sequencing reaction set, and 0 001 units of yeast inorganic pyrophosphatase (4 ng). A wide range of pyrophosphatase activity will work successfully: 0.01 ng to 1 µg of yeast pyrophosphatase per sequencing reaction have been tested with success.

For example, in the annealing reaction the following solution was prepared:

| | |
|---|---|
| mGPL-2 DNA (in 10 mM Tris-HCl pH 7.5, 0.1 mM EDTA) | 7 µl |
| 5X SeqBuf | 2 |
| Primer (New England Biolabs-17mer, 0.5 pm/µl Cat #1211) | 1 |
| | 10 µl |

This solution was heated at 65° C. 2 min, and slow cooled to room temperature.

In the labeling reaction the following solution was prepared:

| | |
|---|---|
| Annealing reaction mixture | 10 µl |
| Dithiothreitol 0.1M | 1 |
| $^{35}$S dATP, New England Nuclear NEG-034H | 1 |
| 3 dNTP (1.5 µM each dTTP, dCTP, 3 µM dITP) | 2 |
| Enzyme mixture (see below) | 2 |
| | 16 µl |

| Enzyme mixture: | |
|---|---|
| Genetically modified T7 DNA polymerase, Δ Lys118-Arg145 | 1 unit/µl |
| Yeast inorganic pyrophosphatase in 20 mM Tris-HCl pH 7.5, 10 mM β-mercaptoethanol, 50 µg/ml bovine serum albumin | 0.01 units µl |

This solution was incubated at room temperature for 5 min.

In the termination reactions the following four reaction mixtures were prepared:

| | G | A | T | C |
|---|---|---|---|---|
| 5X SeqBuf (see above) | 0.6 | 0.6 | 0.6 | 0.6 µl |
| 4dNTPs (3mM each dATP, dTTP, dCTP, and 6 mM dITP) | 0.3 | 0.3 | 0.3 | 0.3 µl |
| H$_2$O | 1.9 | 1.9 | 1.9 | 1.9 µl |
| ddGTP 0.03 mM | 0.2 µl | | | |
| ddATP 0.2 mM | | 0.2 µl | | |
| ddTTP 0.2 mM | | | 0.2 µl | |
| ddCTP 0.2 mM | | | | 0.2 ml |
| | 3 | 3 | 3 | 3 µl |

These termination mixtures were incubated at 37° C for 2 min, and 3 µl aliquots of the labeling reaction added to each termination mixture. The resulting solutions were incubated at 37° C. for 60 min.

Each termination reaction was stopped with 5 µl of 90% formamide, 20 mM EDTA, 0.2% bromophenol-blue, xylene-cyanol, pH 8.0.

The resulting samples were heated at 75° C. for two minutes, loaded onto a polyacrylamide gel (8% polyacrylamide, 0.3% bisacrylamide) in 7M urea, 100 mM Tris-borate, pH 8.9, and electrophoresed at 2000 volts for 2 hours. The gel was fixed in 50% methanol, and 10% acetic acid for 30 min, dried, and used to expose film by autoradiography.

Apparatus

Referring to FIG. 11, apparatus 100, suitable for automated DNA sequencing, includes a reactor 102 including the above described reagents 104, for example, DNA polymerase, manganese or iron ions, chelators and pyrophosphatase. The apparatus is also provided with a gel box 106, for separating DNA products according to their molecular weights, and a gel reading means 108 for detecting the DNA products as they pass through the gel (shown by dashed arrows 107). Further, a computing means 110 is provided to calculate the intensity of bands of DNA products, and the position of the bands relative to one another. If the DNA products are run in one lane, then the computer means is able to compute the DNA sequence from the band intensity and position. Standard computer programs are used to perform this function.

Other embodiments are within the following claims.

We claim:

1. A method for sequencing a strand of DNA, comprising the steps of:

providing said strand hybridized with a primer able to hybridize to said strand, to give an hybridized mixture, incubating said hybridized mixture with four deoxyribonucleoside triphosphates, a DNA polymerase, and a first chain terminating agent, wherein said DNA polymerase causes said primer to be elongated to form a first series of first DNA products differing in the length of the elongated primer, each said first DNA product having a said chain terminating agent at its elongated end, the number of molecules of each said first DNA products being approximately the same for substantially all DNA products differing in length by no more than 20 bases, and providing a second chain terminating agent in said hybridized mixture at a concentration different from said first chain terminating agent, wherein said DNA polymerase causes production of a second series of second DNA products differing in the length of the elongated primer, each said second DNA product having said second chain terminating agent at its elongated end, the number of molecules of each said second DNA products being approximately the same for substantially all second DNA products differing in length from each other by from 1 to 20 bases, and being distinctly different from the number of molecules of all said first DNA products having a length differing by no more than 20 bases from that of said second DNA products.

2. The method of claim 1 further including the steps of:

separating said first and second DNA products by gel permeation according to molecular weight to form a first and second series of bands respectively, each said first or second series band representing a said first or second DNA product, respectively, of a given molecular weight, wherein the intensity of each nearby first series band is approximately the same for substantially all said first series bands, and wherein the intensity of substantially all nearby second series bands is approximately the same, and wherein the intensity of substantially all bands of the first series is distinctly different from the intensity of each nearby band of the second series, and determining the position and intensity of each said first and second series band.

3. The method of claim 1 further comprising the step of:
providing a third chain terminating agent in said hybridized mixture at a concentration different from said first and second chain terminating agents, wherein said polymerase causes production of a third series of third DNA products differing in the length of the elongated primer, each said third DNA product having said third chain terminating agent at its elongated end, the number of molecules of each said third DNA product being approximately the same for substantially all said third DNA products which differ in length by no more than 20 bases, wherein the numbers of molecules of substantially all said first, all said second and all said third DNA products are distinctly different from the numbers of molecules of all those DNA products of a different series which are of lengths differing from them by no more than 20 bases.

4. The method of claim 3 further including the steps of:
separating said first, second and third DNA products by gel permeation according to molecular weight to form a first, second and third series of bands, respectively, each said first, second or third series band representing a said first, second or third DNA product, respectively, of a given molecular weight, wherein the intensity of each nearby first series band is approximately the same for substantially all said first series bands, wherein the intensity of substantially all nearby second series bands is approximately the same, and the intensity of substantially all nearby third series bands is approximately the same, and wherein the intensity of substantially all nearby bands of different series is distinctly different, and
determining the position and intensity of each said band.

5. The method of claim 3 further comprising the step of:
providing in said hybridized mixture a fourth chain terminating agent at a concentration different from said first, second and third chain terminating agents, wherein said DNA polymerase causes production of a fourth series of fourth DNA products differing in the length of the elongated primer, each said fourth DNA product having said fourth chain terminating agent at its elongated end, the number of molecules of each said fourth DNa product being approximately the same or substantially all fourth DNa products differing in length by no more than 20 bases, wherein the number of molecules of substantially all said first, all said second, all said third, and all said fourth series of DNA products is distinctly different from all the number of molecules of those DNa products of a different series which differ in length from them by no more than 20 bases.

6. The method of claim 5, further including the steps of:
separating said first, second, third and fourth DNA products by gel permeation according to molecular weight to form a first, second third and fourth series of bands respectively, each said first, second, third and fourth series band representing a said first, second, third or fourth DNA product of a given molecular weight, wherein each said second, third and fourth series produce second, third and fourth bands, wherein the intensity of substantially all nearby first series bands, or substantially all nearby second series bands, or substantially all nearby third series bands, or substantially all nearby fourth series bands is approximately the same, and wherein the intensity of substantially all nearby bands in a different series is distinctly different, and
determining the position and intensity of each said band.

7. The method of claim 1, 2, 3, 4, 5 or 6 wherein said hybridized mixture is provided with a manganese or iron ion, wherein said ion causes said polymerase to be non-discriminatory for a said chain terminating agent.

8. The method of claim 5 wherein said DNA products are separated according to molecular weight in less than four lanes of a gel.

9. The method of claim 8 wherein the intensity of each band is measured by a gel reading apparatus.

10. The method of claim 1, 2, 3, 4, 5, or 6 wherein each said chain terminating agent is a dideoxynucleoside triphosphate.

11. The method of claim 7, wherein said hybridized mixture is provided with a chelator.

12. The method of claim 11, said chelator being citrate or isocitrate.

13. A method for sequencing a strand of DNA, comprising the steps of:
providing a DNA polymerase, and
incubating said polymerase and said strand of DNA in a solution comprising a manganese ion and a chain terminating agent wherein said ion is provided at a concentration effective for causing production of approximately equal numbers of molecules of these DNA products which differ in size from each other by no more than 20 bases.

14. A kit for sequencing DNA comprising:
a first container comprising a DNA polymerase,
a second container comprising a chain terminating agent, and
a compound comprising a manganese ion.

15. A kit for sequencing DNA comprising:
a first container comprising a DNA polymerase,
a second container comprising a chain terminating agent, and
a compound comprising an iron ion.

16. The kit of claim 14 or 15 wherein said polymerase is a T7-type DNA polymerase, suitable for DNA sequencing, Klenow, or Taq polymerase.

17. The kit of claim 14, 16, or 15, wherein each said chain terminating agent is a dideoxynucleoside triphosphate.

18. The kit of claim 16 further comprising a deoxyribonucleoside triphosphate.

19. The kit of claim 14 further comprising a chelator.

20. The kit of claim 19, said chelator being citrate or isocitrate.

21. A method for sequencing DNA comprising:
providing a DNA polymerase in a reaction medium in which said DNA polymerase is substantially non-discriminating for a chain terminating agent, and
incubating said DNA in said reaction medium with said DNa polymerase, a primer, four deoxyribonucleosie triphosphates and a chain terminating agent to elongate said primer to form a series of DNA products differing in the length of the elongated primer and having said chain terminating agent at the elongated end, the number of molecules of each said DNA product being approximately the same for substantially all those DNA products differing in size by no more than 20 bases.

22. The method of claim 21 wherein said DNA polymerase is a T7-type DNA polymerase provided in a solution comprising manganese ions.

23. The method of claims 7, 13, or 22 wherein said manganese ions are at a concentration between 5 $\mu$M and 20 $\mu$M.

24. A method for sequencing a strand of DNA, comprising the steps of:
  providing said strand hybridized with a primer able to hybridize to said strand, to give a hybridized mixture, and
  incubating said hybridized mixture with four deoxyribonucleoside triphosphates, a DNA polymerase, and a plurality of chain terminating agents in a reaction medium in which said polymerase causes said primer to be elongated to form a series of DNA products differing in the length of the elongated primer, each DNA product having a first said chain terminating agent at its elongated end, wherein the number of molecules of said DNA products is approximately the same for substantially all DNA products differing in length by no more than 20 bases.

25. The method of claim 24, wherein said reaction medium comprises manganese ions.

26. The method of claim 25, wherein said manganese ions are at a concentration between 5 $\mu$M and 20 mM.

27. The method of claim 25, wherein said reaction medium comprises a chelator and manganese ions at a concentration between 0.005 and 100 mM.

28. The method of claim 13 wherein said solution comprises a chelator and said manganese ion is at a concentration between 0.005 nd 100 mM.

29. The method of claim 13 wherein said manganese ion is at a concentration between 5 $\mu$M and 20 mM.

30. The method of claim 1, 2, 3, 4, 5 or 6, wherein said hybridized mixture is provided with a manganese ion, wherein said ion causes said polymerase to be non-discriminating for a said chain terminating agent.

31. The method of claim 1, 2, 3, 4, 5 or 6, wherein said DNA polymerase is selected from the group consisting of the large fragment of E. coli DNA polymerase I and Taq polymerase.

32. The method of claim 1, 2, 3, 4, 5 or 6, wherein said DNA polymerase is a T7-type DNA polymerase.

33. A method for sequencing a strand of DNA, comprising the steps of:
  providing a DNA polymerase, and
  incubating said polymerase and said strand of DNA in a solution comprising an iron ion and a chain terminating agent wherein said ion is provided at a concentration effective for causing production of approximately equal numbers of molecules of DNA products differing in size by no more than 20 bases.

34. A method for sequencing a strand of DNA, comprising the steps of:
  providing said strand hybridized with a primer able to hybridize to said strand to give an hybridized mixture,
  incubating said hybridized mixture with four deoxyribonucleoside triphosphates, a DNA polymerase, and a plurality of different chain terminating agents each capable of terminating the DNa synthesis at a different nucleotide base, to cause said primer to be elongated to form a series of DNA products differing in length with each DNA product having a chain terminating agent at its elongated end, the amount of each said chain terminating agent being distinctly different from that of each other chain terminating agent, and said incubation causing the total amount of said series terminating with one chain terminating agent to be distinctly different from the total amount of said series terminating with each different chain terminating agent, and
  separating said series according to length, whereby the DNA products of approximately the same length containing one chain terminating agent are distinctly different in amount from those containing any other chain terminating agent.

* * * * *

UNITED STATES PATENT AND TRADEMARK OFFICE
CERTIFICATE OF CORRECTION

PATENT NO. : 4,962,020                                          Page 1 of 3

DATED      : October 9, 1990

INVENTOR(S) : Tabor et al.

It is certified that error appears in the above-identified patent and that said Letters Patent is hereby corrected as shown below:

In Other Publications; page 2; "Wong et al." "19087" should be --1987--

In Other Publications; page 4; #7 to the end are all repeats of page 3 please cancel them.

In Other Publications; page 3; "Kunkel et al" "5817" should be --5718--

Col. 1; line 45; "non uniform" should be --non-uniform--
       line 60; insert --.-- after "gel"
       line 67; insert --.-- after "primer"

Col. 4; line 59; delete the hyphen after "position"

Col. 7; line 58; insert --:-- after "84"
       line 67; insett -- - -- between "pGP5 8"

Col. 8; line 9; insert -- - -- between "T7 type"

Col. 9; line 10; insert --.-- after "Mn"
       line 48; "proc." should be --Proc.--

Col. 10; line 63; "nGP5-2" should be --mGP5-2--

UNITED STATES PATENT AND TRADEMARK OFFICE
CERTIFICATE OF CORRECTION

PATENT NO. : 4,962,020

DATED : October 9, 1990

INVENTOR(S) : Tabor et al.

It is certified that error appears in the above-identified patent and that said Letters Patent is hereby corrected as shown below:

Col. 11; line 5; "DNa" should be --DNA--
       line 11; "plagues" should be --plaques--
       line 23; delete --,-- and insert --.-- after "gene 5"
       line 25; delete hyphens before and after "-m-"
       line 34; insert --.-- after "deletion"
       line 62; "sequencing" should be -- Sequencing--

Col. 12; line 25; delete "m" from "mmodified"

Col. 15; line 1; "v" should be -'v'--
       line 35; insert -- - -- between "acid insoluble"

Col. 17; line 6; "0 001" should be --0.001--

Col. 19; line 53; "DNa" should be --DNA--
       line 55; "DNa" should be --DNA--
       line 60; "DNa" should be --DNA--

Col. 20; line 68; "DNa" should be -- DNA--

UNITED STATES PATENT AND TRADEMARK OFFICE
CERTIFICATE OF CORRECTION

PATENT NO. : 4,962,020

DATED : October 9, 1990

INVENTOR(S) : Tabor et al.

It is certified that error appears in the above-identified patent and that said Letters Patent is hereby corrected as shown below:

Col. 21; line 1; "cleosie" should be --cleoside--

Col. 22; line 28: "DNa should be --DNA--

Signed and Sealed this

Thirty-first Day of March, 1992

Attest:

HARRY F. MANBECK, JR.

*Attesting Officer*     *Commissioner of Patents and Trademarks*